US011422136B2

(12) United States Patent
Xie et al.

(10) Patent No.: US 11,422,136 B2
(45) Date of Patent: Aug. 23, 2022

(54) DETECTION OF SYMMETRICAL DIMETHYLARGININE

(71) Applicant: IDEXX LABORATORIES, INC., Westbrook, ME (US)

(72) Inventors: Hongzhi Xie, Falmouth, ME (US); Sreenivasa Rao Ramisetty, South Portland, ME (US); Murthy V S N Yerramilli, Falmouth, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 375 days.

(21) Appl. No.: 16/165,337

(22) Filed: Oct. 19, 2018

(65) Prior Publication Data

US 2019/0120856 A1 Apr. 25, 2019

Related U.S. Application Data

(60) Provisional application No. 62/599,117, filed on Dec. 15, 2017, provisional application No. 62/574,592, filed on Oct. 19, 2017.

(51) Int. Cl.
*G01N 33/68* (2006.01)
*G01N 33/563* (2006.01)
*G01N 33/60* (2006.01)
*G01N 33/58* (2006.01)

(52) U.S. Cl.
CPC ....... *G01N 33/6893* (2013.01); *G01N 33/563* (2013.01); *G01N 33/6812* (2013.01); *G01N 33/582* (2013.01); *G01N 33/583* (2013.01); *G01N 33/60* (2013.01)

(58) Field of Classification Search
CPC .. G01N 33/563; G01N 33/582; G01N 33/583; G01N 33/60; G01N 33/6812; G01N 33/6893
See application file for complete search history.

(56) References Cited

U.S. PATENT DOCUMENTS

| | | | |
|---|---|---|---|
| 3,875,011 A | 4/1975 | Rubenstein et al. | |
| 4,485,177 A | 11/1984 | Siedel et al. | |
| 4,578,361 A | 3/1986 | Siedel et al. | |
| 4,686,181 A | 8/1987 | Dona | |
| 4,818,703 A | 4/1989 | Pizzolante | |
| 5,318,680 A | 6/1994 | Fishman et al. | |
| 5,726,010 A | 3/1998 | Clark | |
| 6,358,699 B1 | 3/2002 | Balint et al. | |
| 6,455,288 B1 | 9/2002 | Jakobovits et al. | |
| 6,699,673 B2 | 3/2004 | Aletta | |
| 6,706,742 B2 | 3/2004 | Nanteuil et al. | |
| 6,720,188 B2 | 4/2004 | Kaddurah-Daouk et al. | |
| 6,736,957 B1 | 5/2004 | Forrow et al. | |
| 7,611,844 B2 | 11/2009 | Lin et al. | |
| 8,481,690 B2 | 7/2013 | Yerramilli et al. | |
| 8,628,936 B2 | 1/2014 | Turner et al. | |
| 9,091,684 B2 | 7/2015 | Yerramilli et al. | |
| 9,891,223 B2 | 2/2018 | Beaulieu et al. | |
| 9,970,927 B2 | 5/2018 | Yerramilli et al. | |
| 2004/0214252 A1 | 10/2004 | Lin et al. | |
| 2004/0242723 A1 | 12/2004 | Jin et al. | |
| 2005/0148029 A1 | 7/2005 | Buechler et al. | |
| 2005/0266574 A1 | 12/2005 | Kosaka | |
| 2006/0040408 A1* | 2/2006 | Jones | G01N 33/558 436/518 |
| 2006/0094122 A1 | 5/2006 | Boeger et al. | |
| 2006/0201805 A1 | 9/2006 | Forrow et al. | |
| 2010/0035274 A1* | 2/2010 | Murthy | C07K 16/44 435/7.1 |
| 2012/0129265 A1 | 5/2012 | Lundin et al. | |
| 2012/0214978 A1 | 8/2012 | Lele | |
| 2014/0038203 A1 | 2/2014 | Arthur et al. | |
| 2014/0221616 A1 | 8/2014 | Donahue et al. | |
| 2014/0315216 A1 | 10/2014 | Chan et al. | |
| 2016/0187324 A1 | 6/2016 | Bieniarz et al. | |
| 2016/0187348 A1 | 6/2016 | Yerramilli et al. | |
| 2016/0245801 A1 | 8/2016 | Yerramilli et al. | |
| 2019/0120856 A1 | 5/2019 | Xie et al. | |

FOREIGN PATENT DOCUMENTS

| | | |
|---|---|---|
| CN | 101865911 A | 10/2010 |
| CN | 102628868 A | 8/2012 |
| CN | 101587118 A | 9/2012 |

(Continued)

OTHER PUBLICATIONS

Englebienne, "Immune and Receptor Assays in Theory and Practice," CRC Press, 2000, p. 308.*
A printout "Imject® Maleimide-Activated mcKLH" retrieved from https://assets.thermofisher.com /TFS-Assets/LSG/manuals/MAN0011384_Imject_Maleimide_Activ_mcKLH_UG.pdf on Feb. 10, 2021.*
A printout "SM(PEG)12 (PEGylated, long-chain SMCC crosslinker)" retrieved from https://www.thermofisher.com/order/catalog/product/22112#/22112 on Feb. 5, 2021.*
Richard, et al., "Arginine methylation regulates IL-2 gene expression: a role for protein arginine methylliansferase 5 (PRMT5)," Biochem J., 388:379-386 (2005).
Mahler, et al., "Identification of a SmD3 epitope with a single symmetrical dimethylation of an arginine residue as a specific target of a subpopulation of anti-Sm antibodies," Arthritis Research & Therapy, 7:19-29 (2004).

(Continued)

*Primary Examiner* — Galina M. Yakovleva
(74) *Attorney, Agent, or Firm* — McDonnell Boehnen Hulbert & Bergthoff LLP

(57) ABSTRACT

The disclosure generally relates to the detection of symmetrical dimethylarginine (SDMA). More particularly, the disclosure relates to the detection of SDMA using a solid phase. The disclosure provides devices, reagents, kits and methods for detecting symmetrical dimethyl arginine (SDMA) in sample, such as a biological sample from an animal. The method includes detecting the presence or amount of SDMA in the sample by using an immunoassay format, such as a competitive immunoassay. The assay includes the use of antibodies to SDMA that are specific for SDMA and that have less affinity for other arginine derivatives.

22 Claims, 13 Drawing Sheets

(56) References Cited

FOREIGN PATENT DOCUMENTS

| | | |
|---|---|---|
| CN | 101598727 B | 10/2012 |
| DE | 102005060057 A1 | 6/2007 |
| EP | 1666884 | 6/2006 |
| EP | 2612147 B1 | 3/2016 |
| JP | 2012112785 A | 6/2012 |
| WO | 9634271 A1 | 10/1996 |
| WO | 98/49199 | 11/1998 |
| WO | 2002/04465 A1 | 1/2002 |
| WO | 0204950 A2 | 1/2002 |
| WO | 2002/014873 | 2/2002 |
| WO | 2004/046314 | 6/2004 |
| WO | 2006/078813 | 7/2006 |
| WO | 2006/078813 A2 | 7/2006 |
| WO | 2007/074864 | 7/2007 |
| WO | 2007/074864 A1 | 7/2007 |
| WO | 2016/134251 A1 | 8/2016 |

OTHER PUBLICATIONS

Brahms, et al., "The C-terminal RG Dipeptide Repeats of the Spliceosomal Sm Proteins D1 and D3 contain Symmetrical Dimethylarginines, Which Form a Major B-cell epitope for Anti-Sm Autoantibodies," The Journal of Biological Chemistry, 275:17122-17129 (2000).
Boisvert, et al., "Symmetrical dimethylarginine methylation is required for the localization of SMN in Cajal bodies and pre-mRNA splicing," The Journal of Cell Biology, 159:957-969 (2002).
Boisvert, Francois-Michel, "A role for arginine methylation in DNA repair," Dissertation abstracts International, 68:34 (2005).
Bode-Böger, et al., "Symmetrical dimethylarginine: A New combined Parameter for renal Function and extent of Coronary Artery Disease," Journal of the American Society of Nephrology; 17:1128-1134 (2006).
Schnabel, et al., "Asymmetric Dimethylarginine and the Risk of Cardiovascular events and Death in Patients with Coronary Artery Disease—results from the AtheroGene Study," Circulation Research 97:1-7(2005).
Böger, Rainer, "Asymmetric dimethylarginine (ADMA): A novel risk marker in cardiovascular medicine and beyond," Annals of Medicine, 38:126-136 (2006).
Schulze, et al., "Determination of a reference value for NG, NG-dimethyl-L-arginine in 500 subjects," European Journal of Clinical Investigation, 35:622-626 (2005).
Kielstein, et al., "Symmetric dimethylarginine (SDMA) as endogenous marker of renal function—a meta-analysis," Nephrol Dial. Transplant, 21:2446-2451 (2006).
Schulze, et al., "Determination of asymmetric dimethylarginine (ADMA) using a novel ELISA assay," Clin. Chem. Lab Med. 42:1377-1383 (2004).
ADMA—ELISA, Enzyme Immunoassay for the quantitative Determination of Endogenous Asymmetric Dimethylarginine (ADMA) in Serum or Plasma, (2007).
SDMA—ELISA, Enzyme Immunoassay for the quantitative Determination of Endogenous Symmetric Dimethylarginine (SDMA) in Serum or Plasma, p. 1-16 (2008).
Liu, et al., "New Procedures for Preparation and Isolation of Conjugates of Proteins and a Synthetic Copolymer of D-Amino Acids and Immunochemical Characterization of Such Conjugates," Biochemistry 18:690 (1979).
Kitagawa, et al., "Preparation and characterization of Heterobifunctional Cross-linking Reagents for Protein Modificiations," Chem. Pharm. Bull. 29:1130-1135 (1981).
Duncan, et al., "A New Reagent Which may be Used to Introduce Sulfhydryl Groups into Proteins, and Its use in the Preparation of Conjugates for Immunoassay," Anal. Biochem 132:68-73 (1983).
Palmer, et al., "Reduction and Reoxidation of a Critical Disulfide Bond in the Rabbit Antibody Molecule," J. Biol. Chem 238:2393 (1963).

Bedford, et al., "Arginine Methylation: An Emerging Regulator of Protein Function," Mol. Cell, 18:263-272 (2005).
Blackwell, et al., "Biological variation of asymmetric dimethylarginine and related arginine metabolites and analytical performance goals for their measurement in human plasma," Eur J. Clin Invest. 37:364-371 (2007).
Nijveldt, et al., "Handling of asymmetrical dimethylarginine and symmetrical dimethylarginine by the rat kidney under basal conditions and during endotoxaemia," Nephrol Dial. Transplant 18:2542-2550 (2003).
Boisvert, et al., "A Proteomic Analysis of Arginine-Methylated Protein Complexes," Molecular & Cellular Proteomics, 2:1319-1329(2003).
Fleck, et al., "Serum concentrations of asymmetric (ADMA) and symmetric (SDMA) dimethylarginine in renal failure patients," Kidney International, 59:14-18 (2001).
Biovendor Research and Diagnostic Products: "Enzyme Immunoassay for the Quantitative Determination of Endogenous Symmetric Dimethylarginine (SDMA) in Serum or Plasma", SDMA ELISA, Instructions for use, p. 1-13 (2008).
Upstate cell signaling solutions, "Certificate of Analysis for Anti-dimethyl-Arginine, symmetric (SYM11), "rabbit polyclonal IgG; downloaded May 24, 2011 from www.millipore.com.
Upstate cell signaling solutions, "Certificate of Analysis for Anti-dimethyl-Arginine, symmetric (SYM10), "rabbit antiserum; downloaded May 24, 2011 from www.millipore.com.
"SDMA (human) ELISA kit," Enzo Life Sciences, Version 01: Dec. 8, 2009.
Moesgaard, et al., "Effects of breed, gender, exercise and white-coat effect on markers of endothelial function in dogs," Research in Veterinary Science, 82:409-418 (2007).
Product Information List retrieved from DLD Diagnostika GmbH—Online in Jan. 25, 2011.
Goodrow et al., "Strategies for Immunoassay Hapten Design," in Immunoanalysis of Agrochemicals; Nelson, J., et al.; ACS Symposium Series, vol. 586, Chapter 9, pp. 119-139 (1995).
Honda, et al. "Analysis of sDMA modifications of PIWI proteins," Methods in Molecular Biology, vol. 1093, pp. 137-148 (2013).
Kaptein, "Thyroid Hormone Metabolism and Thyroid Diseases in Chronic Renal Failure," Endocrine Reviews, vol. 17, No. 1, pp. 45-63 (1996).
Peterson et al., "Using hapten design to discover therapeutic monoclonal antibodies for treating methamphetamine abuse," J. Pharmacal. Exp Ther., vol. 322, No. 1, pp. 30-39 (2007).
Pravetoni et al., "Structurally distinct nicotine immunogens elicit antibodies with non-overlapping specificities," Biochem. Pharmacal., Feb. 15, 2012; vol. 83, No. 4, pp. 543-550, Published online Nov. 15, 2011.
Szurdoki et al., "Important Factors in Hapten Design and Enzyme-Linked Immunosorbent Assay Development," in Immunoanalysis of Agrochemicals; Nelson, J., et al.; ACS Symposium Series, vol. 586, Chapter 4, pp. 39-63 (1995).
Williams T., "Chronic kidney disease in cats with hyperthyroidism," Clin Brief Sep. 2015:10-12.
Jepson R. Feline hyperthyroidism and chronic kidney disease. In: Proceedings from the BSAVA Congress; Apr. 9-12, 2015; Birmingham, UK.
Mian, I.S. et al., "Structure, Function and Properties of Antibody Binding Sites," J. Mol. Biol. 217, pp. 133-15 (1991).
King, "Sensitivity of immunoassays for detecting cross-reactivity of homologous venom proteins of yellow jackets," J. Allergy Clin. Immunol, 79(1): 113-20 (1987).
Lerner et al., "Monoclonal antibodies to nucleic acid-containing cellular constituents: Probes for molecular biology and autoimmune disease," Proc. Natl. Acad. Sci. USA., 78(5): 2737-41 (1981).
Fenney et al., "Cytoplasmic Assembly and Nuclear Accumulation of Mature Small Nuclear Ribonucleoprotein Particles," J Biol Chem, 264(10): 5776-83 (1989).
Xu et al., "The C-terminal domain of coilin interacts with Sm proteins and U snRNPs," Chromosoma, 114(3): 155-66 (2005).
Harlow, E. and Lane, D.P. Chapter 5: Immunization and Chapter 14: Immunoassays. In Antibodies: A Laboratory Manual, Cold Spring Harbor Laboratory, pp. 53-54, 72-87, and 563-604 (1988).

(56) References Cited

OTHER PUBLICATIONS

Chang Hwa Lee, "Estimation of GFR", The Korean Journal of Internal Medicine, 2012, vol. 83, pp. 455-457.
Stevens, et al., "Assessing Kidney Function—Measured and Estimated Glomerular Filtration Rate" NEJM, 354:2473-2483 (2006).
Jepson RE et al., "Plasma Asymmetric Dimethylarginine, Symmetric Dimethylarginine, L-Arginine, and Nitrite/Nitrate Concentrations in Cats with Chronic Kidney Disease and Hypertension." J Vet Intern Med, 22:317-324 (2008).
Immunodiagnostik AG—SDMA ELISA Kit for the Determination of SDMA in Human EDT A-Plasma and Serum—Instructions (2009).
Immunodiagnostik AG—SDMA ELISA Kit for the Determination of SDMA in Human EDT A-Plasma and Serum—Instructions (2012).
Nabity, et al., "Symmetric Dimethylarginine Assay Validation, Stability, and Evaluation as a Marker for the Early Detection of Chronic Kidney Disease in Dogs," J Vet Intern Med. 29(4):1036-44 (2015).
Chapter 5: Concepts. In The Immunoassay Handbook, Wild, D. Ed. Nature Publishing Group: United Kingdom, 2nd Edition, pp. 78-86 (2001).
Fleck et al., "Serum concentrations of asymmetric (ADMA) and symmetric (SOMA) dimethylarginine in patients with chronic kidney diseases", Clinica Chimica Acta, 336:1-12 (2003).
Nabity et al., "Correlation of symmetric dimethylarginine with glomerular filtration rate in dogs with chronic pregressive renal disease," J Vet Intern Med., May 2013, 27(3):733.
Kielstein et al., "SDMA is an early marker of change in GFR after living-related kidney donation," Nephrology Dialysis Transplantation, Jul. 2011, pp. 324-328, vol. 26, No. 1.
Cooper, A. J. et al. "Cyclic Forms of the alpha-Keio Acid Analogs of Arginine, Citrulline, Homoarginine, and Homocilrulline," J. Biol. Chem., Aug. 10, vol. 253, No. 15, pp. 5407-5410 (1978).
Dobashi et al., "An automated analyzer for methylated arginines in rat plasma by high-performance liquid chromatography with post-column fluorescence reaction," Analyst, vol. 127, pp. 54-59 (2002).
Vanholder et al., "Reviewon uremic toxins: Classification, concentration, and interindividual variability," Kidney International, May 1, 2003, pp. 1934-1943, vol. 63.
Greene, TW et al., "Chapter 5—Protection for the Carboxyl Group," Protective Groups in Organic Synthesis, 3rd Edition, 1999, pp. 369-453.
Greene, TW et al., "Chapter 6—Protection for the Thiel Group," Protective Groups in Organic Synthesis, 3rd Edition 1999, pp. 454-493.
Greene, TW et al., "Chapter 7—Protection for the Amino Group," Protective Groups in Organic Synthesis, 3rd Edition, 1999, pp. 494-653.
Koch et al., "Regulation and Prognostic Relevance of Symmetric Dimethylarginine Serum Concentrations in Critical Illness and Sepsis," Mediators of Inflammation, Jun. 27, 2013, pp. 1-8, vol. 2013.
Levey et al., "Glomerular filtration rate measurements in clinical trials: Modification of Diet in Renal Disease Study 28 3roup and the Diabetes Control and Complications Trial Research Group" Journal of the American Society of Nephrology, 1993, pp. 1159-1171, vol. 4, No. 5.
MacAllister et al., "Concentration of dimethyl-L-arginine in the plasma of patients with end-stage renal failure," Nephrology Dialysis Transplantation, Dec. 11, 1996, pp. 2449-2452, vol. 11.
Midttun et al., "High-throughput, low-volume multianalyte quantification of plasma metabolites related to one-carbon 32 metabolism using HPLC-MS/MS," Analytical and Bioanalytical Chemistry, Dec. 13, 2012, pp. 2009-2017, vol. 405.
Nabity et al., "Day-to-Day Variation of the Urine Protein: Creatinine Ratio in Female Dogs with Stable Glomerular Proteinuria Caused by X-Linked Hereditary Nephropathy," J Vet Intern Med., 2007, pp. 425-430, vol. 21.

Perrone et al., "Utility of Radioisotopic Filtration Markers in Chronic Renal Insufficiency: Simultaneous Comparison of 1251-lothalamate, 169Yb-DTPA, 99mTc-DTPA, and Inulin," Am. J. Kidney Disease, 1990, pp. 224-235, vol. 16, No. 3.
Duerksen, P.J. et al., "Immobilization of Proteins Via Arginine Residues," Anal. Biochem., vol. 160, pp. 444-454 (1987).
Ogawa et al., "Metabolism of Ng, NG- and NG, NG-Dimethylarginine in rats," Arch. Biochem. Biophys., vol. 252, No. 2, pp. 526-537 (1987).
Pettersson et al., "Determination of dimethylated arginines in human plasma by high-performance liquid chromatography," Journal of Chromatography B, vol. 692, pp. 257-262, (1997).
Pi et al., "Improved method for simultaneous determination of L-arginine and its mono- and dimethylated metabolites in biological samples by high-performance liquid chromatography," Journal of Chromatography B, vol. 742, pp. 199-203, (2000).
Patch D. et al. Abstract of :High Throughput Immunoassay for Kidney Function Biomarker Symmetric Dimethylarginine {SOMA) Clin Chem (2015) pp. 3-3. XP055487566—Retrieved from the Internet: URL:https:/lwww.acc.org/science-and-pract ice/annual-meeting-abstracts-archive/2015-annual-meeting-abstracts [retrieved on 018-06-25].
Hall et al., "Comparison of Serum Concentrations of Symmetric Dimethylarginine and Creatinine as Kidney Function Biomarkers in Cats with Chronic Kidney Disease," J Vet Intern Med (2014), 28:1676-1683.
Opiate 200 Ng (OP2) Chemistry Information Sheet, Aug. 2010, Beckman Coulter Inc.
COCM Chemistry Information Sheet, Aug. 2010, Beckman Coulter Inc.
Emil® 2000 Carbamazepine Chemistry Information Sheet, Sep. 2010, Beckman Coulter Inc.
Emil® 2000 Vancomycin Chemistry Information Sheet, Sep. 2010, Beckman Coulter Inc.
Schwarzenbolz, U. et al., "On the reaction of glyoxal with proteins," Zeitschrifl tor Lebensmitteluntersuchung undrorschung A, vol. 205, pp. 121-124 (1997).
A printout retrieved from http://www.science.uwaterloo.ca/-cchieh/cact/c120/bondel.html on Apr. 23, 2018.
A printout P1709 retrieved from https://www.sigmaaldrich.com/catalog/product/sigma/p1709?1ang =en®ion=US on Apr. 23, 2018.
A printout SIA (succinimidyl iodoacetate) retrieved from https://www.thermofisher.com/order/catalog/product/22349 on Apr. 23, 2018.
Sopio, R. et al., "Reaction of 3-deoxypentosulose with N-methyl- and N, N-dimethylguanidine as model reagents for protein-bound arginine and for creatine," Z. Lebensm. Unters Forsch. A., vol. 201, pp. 381-386(1995).
Stuhlinger et al., "Relationship Between Insulin Resistance and an Endogenous Nitric Oxide Synthase Inhibitor," J. Am. Med. Assoc., vol. 287, No. 11, pp. 1420-1426 (2002).
Takahashi, Kenji, "The Reaction of Phenylglyoxal with Arginine Residues in Proteins," J. Biol. Chem., vol. 243, No. 23, pp. 6171-6179 (1968).
Teerlink et al., "Determination of Arginine, Asymmetric Dimethylarginine, and Symmetric Dimethylarginine in Human Plasma and other Biological Samples by High-Performance Liquid Chromatography," Anal. Biochem., vol. 303, pp. 131-137 (2002).
Vishwanathan et al., "Determination of arginine and methylated arginines in human plasma by liquid chromatography-tandem mass spectrometry," Journal of Chromatography B, vol. 748, pp. 157-166 (2000).
Cooke, J.P., "Asymmetrical Dimethyolarginine: The Uber Marker? ," Circulation, vol. 109, pp. 1813-1818 (2004).
Acchione et al. "Impact of linker and conjugation chemistry on antigen binding, Fc receptor binding and thermal stability of model antibody-drug conjugates" Landes Bioscience, vol. 4, No. 3, pp. 362-372, 2012.
Bioconjugation Technical Handbook. Thermo Fisher Scientific. COL05005, 2015.
Finco DR, et al., "Relationship between plasma creatinine concentration and glomerular filtration rate in dogs." Journal Of Veterinary Pharmacology and Therapeutics 18: 418-421 (1995).

(56) References Cited

OTHER PUBLICATIONS

Fliser D, et al., "Asymmetric dimethylarginine and progression of chronic kidney disease: The mild to moderate kidney disease stud." Journal of the American Society of Nephrology 16: 2456-2461 (2005).
Shreder, K. Synthetic Haptens as Probes of Antibody Response and Immunorecognition. Methods, 20, pp. 372-379 2000).
Baburaj, K. et al., "HOCGO and DMACGO. Two coumarin derived alpha-dicarbonyls suitable as pH and polarity sensitive fluorescent reporters for proteins that can be targeted at reactive arginines," Biochim. Biophys. Acta, vol. 1199, pp. 253-265 (1994).
Bode-Boger, S.M. et al., "Elevated L-Arginine/Dimethylarginine Ratio Contributes to Enhanced Systemic NO Production by Dietary L-Arginine in Hypercholesterolemic Rabbits," Biochem. Biophys. Res. Commun., vol. 219, pp. 598-603 (1996).
Chen et al., "Determination of NG, NG-dimethylarginine in human plasma by high-performance liquid chromatography," Journal of Chromatography B, vol. 692, pp. 467-471 (1997).

\* cited by examiner

Step 3: SPDP Activation of HRP and Reduction by DTT/TCEP

Step 4: Conjugation of SMCC-Mab and Sulfhydryl-Activated HRP

DETECTION OF SYMMETRICAL DIMETHYLARGININE

CROSS-REFERENCE TO RELATED APPLICATIONS

This application claims priority to U.S. provisional patent application Ser. No. 62/574,592, filed Oct. 19, 2017 and U.S. provisional patent application Ser. No. 62/599,117, filed Dec. 15, 2017, each of which is incorporated by reference herein in its entirety.

BACKGROUND

Field of the Disclosure

The disclosure generally relates to the detection of symmetrical dimethylarginine (SDMA). More particularly, the disclosure relates to the detection of SDMA using a solid phase.

Related Art

The detection of free SDMA in a biological sample from an animal can provide an indication of renal function in the animal. Renal diseases and disorders (e.g., kidney impairment, renal insufficiency, chronic kidney disease, glomerulonephritis, diabetic nephropathy, interstitial nephritis, polycystic kidney disease, and hypertensive kidney disease) tend to decrease overall renal function, including GFR (Glomerular Filtration Rate), and can be diagnosed in a number of ways, including use of common renal markers creatinine and BUN. By comparing the level of SDMA, BUN and creatinine in healthy and diseased animals, the level of SDMA in a sample can be related to the disease state of the animal. Accordingly, "healthy" animals showing normal (reference range) creatinine and BUN will have lower SDMA levels than those of diseased animals. In general, animals suffering from a renal disorder/disease will have higher serum SDMA levels than animals with normal renal function. In healthy humans, plasma SDMA levels typically range from 0.3-0.7 µmol/l (J Am Soc Nephrol (2006) 17: 1128-1134; Eur J Clin Invest. 2007 June; 37(5): 364-371. Nephrol Dial Transplant (2003) 18: 2542-2550; Nephrol Dial Transplant (2006) 21: 2446-2451; Kidney International, (2001) 59 (78): S14-S18).

Similarly, the level of free SDMA in a biological sample can be used as a marker of cardiac disease in the animal. The level of SDMA in the sample can be compared to levels of known markers for cardiac disease to determine a cut-off range for diagnosing cardiac disease (J Am Soc Nephrol (2006) 17:1128-1134).

Accordingly, the inventors have identified a need in the art for accurately and efficiently determining SDMA in samples from humans and other animals.

SUMMARY

In one aspect, the disclosure is directed to a device including a solid matrix, such as a porous matrix, having a particle non-diffusively bound thereto, wherein the particle includes a capture reagent including an analog of an analyte or a derivative of the analyte covalently attached to a protein that is attached to the particle. In various embodiments, the protein may be covalently or non-covalently attached to the particle. The protein may be one or more one of Bovine Serum Albumin (BSA), ovalbumin, Keyhole Limpet Hemocyanin (KLH), and Glucose-6-Phosphate Dehydrogenase (G6PDH). The non-covalent attachment of the protein to the particle may be more tolerant to surfactants or high salt concentrations than the non-covalent attachment of BSA, ovalbumin or KLH. The derivative may be an arginine derivative, such as a methylated arginine derivative, for example asymmetrical dimethylarginine (ADMA), L-arginine, N-methylarginine (MMA), acylated ADMA, acylated L-arginine, and acylated MMA. The matrix may be arranged in a cartridge or housing.

In another aspect, the disclosure is directed to a capture reagent including an analog of N-methylarginine (MMA) or acylated MMA attached to a particle. In various embodiments, the analog may be bound to the particle through a linker. The analog may be covalently attached to a protein that is attached to a particle, and the protein may be covalently or non-covalently attached to the particle. The protein may be at least one of Bovine Serum Albumin (BSA), ovalbumin, Keyhole Limpet Hemocyanin (KLH), and Glucose-6-Phosphate Dehydrogenase (G6PDH). The linker may include the following structure:

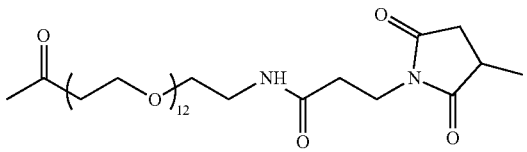

and the capture reagent may be:

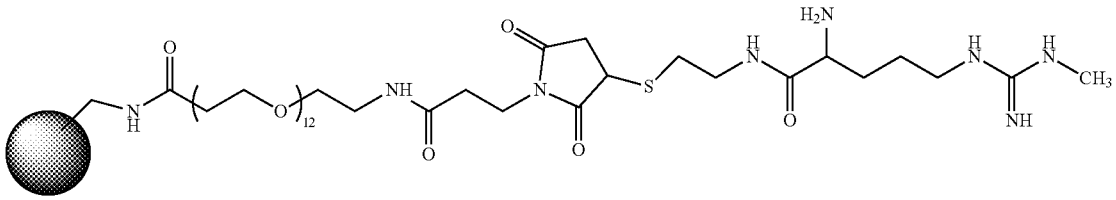

In a further aspect the disclosure is directed to a method of determining symmetrical dimethyl arginine (SDMA) in a sample. The method includes (a) forming a mixture including the sample and a labeled conjugate including an anti-SDMA antibody conjugated to a label; (b) contacting the mixture with the device including an analog of a methylated arginine derivative and a solid support or solid matrix, (c) washing the solid support or matrix to remove conjugate that is not bound to the solid matrix; measuring the amount of the label associated with the solid support or matrix to determine the presence or amount of SDMA in the sample.

In various embodiments, the mixture may be contacted with the device having SDMA as part of the capture reagent and the anti-SDMA antibody having less affinity for the arginine derivative than the affinity for SDMA. For example, the affinity of the anti-SDMA antibody for the arginine derivative may be less than about 25%, less than about 10%, less than about 5%, less than about 1%, less than about 0.1%, less than about 0.01%, or less than about 0.001% of the affinity of the antibody for SDMA.

In yet another aspect, the disclosure is directed to a method of determining symmetrical dimethyl arginine (SDMA) in a sample. The method includes, (a) forming a mixture including the sample and a labeled conjugate including an anti-SDMA antibody conjugated to a label; contacting the mixture with a solid matrix including the capture reagent of including a methylated arginine derivative as described herein; (c) washing the solid matrix to remove conjugate that is not bound to the solid matrix; and measuring the amount of the label associated with the solid matrix to determine the presence or amount of SDMA in the sample.

Still further, the disclosure is directed to a kit for determining SDMA in a sample including the device of the disclosure and a conjugate including an anti-SDMA antibody conjugated to a label, wherein the affinity of the anti-SDMA antibody for a capture reagent is less than about 25% (e.g., about 10%, about 5%, about 1%, about 0.1%, about 0.01% or about 0.001%) of the affinity of the antibody for SDMA.

In yet another aspect, the disclosure is directed to a kit for determining SDMA in a sample including a solid matrix including the capture reagent including a methylated arginine derivative and a conjugate including an anti-SDMA antibody conjugated to a label, wherein the affinity of the anti-SDMA antibody for the capture reagent is less than about 25% (e.g., about 10%, about 5%, about 1%, about 0.1%, about 0.01% or about 0.001%) of the affinity of the antibody for SDMA.

Even further, the disclosure is directed to a method of reducing or eliminating serum-plasma bias in an immunoassay for symmetrical dimethyl arginine (SDMA) in a serum sample or plasma sample. The method includes (a) forming a mixture including the sample and a labeled conjugate including an anti-SDMA antibody conjugated to a label; (b) contacting the mixture with a solid matrix including the solid phase including a arginine derivative as described herein, wherein the protein is non-covalently attached to the particle, wherein the affinity of the anti-SDMA antibody for the arginine derivative is less than about 25% (e.g., about 10%, about 5%, about 1%, about 0.1%, about 0.01% or about 0.001%) of the affinity of the antibody for SDMA; (c) washing the solid matrix to remove conjugate that is not bound to the solid matrix; and (d) measuring the amount of the label associated with the solid matrix to determine the presence or amount of the SDMA in the sample.

In another aspect, the disclosure is directed to a solid phase including and analog of a methylated arginine derivative, such as N-methylarginine (MMA) or acylated MMA, covalently attached to G6PDH that is non-covalently attached to a particle. The solid phase may include a porous matrix, which may be mounted in a housing. An anti-SDMA antibody may be bound to the analog, wherein the antibody has less affinity for the analog than it has for SDMA. For example, the affinity of the anti-SDMA antibody for the analog is less than about 25% (e.g., about 10%, about 5%, about 1%, about 0.1%, about 0.01% or about 0.001%) of the affinity of the antibody for SDMA. The anti-SDMA antibody may be labeled.

In another aspect, the disclosure is directed to a composition including an analog of of a methylated arginine derivative, such as N-methylarginine (MMA) or acylated MMA, immobilized on a solid matrix, wherein the analog is complexed with an anti-SDMA antibody. The antibody the antibody may have affinity for the immobilized analog than it has for SDMA in solution. For example, the affinity of the anti-SDMA antibody for the immobilized analog may be less than about 25% (e.g., about 10%, about 5%, about 1%, about 0.1%, about 0.01% or about 0.001%) of the affinity of the antibody for SDMA in solution. The the anti-SDMA antibody may be labeled. The analog may be covalently attached to a protein. The protein may be one or more of Bovine Serum Albumin (BSA), ovalbumin, Keyhole Limpet Hemocyanin (KLH), and Glucose-6-Phosphate Dehydrogenase (G6PDH). The protein may be non-covalently attached to the solid matrix, wherein the protein may be non-covalently attached to a particle, which is non-diffusively bound to the solid matrix.

In a further aspect, the disclosure is directed to a method of reducing or eliminating serum-plasma bias in an immunoassay for an analyte in serum or plasma sample. The method includes (a) forming a mixture including the sample and a labeled conjugate including an anti-analyte antibody conjugated to a label; (b) contacting the mixture with a device including solid matrix including a particle non-diffusively bound thereto, wherein the particle includes a capture reagent including an analyte analog covalently attached to a protein that is attached to a particle, wherein the affinity of the anti-analyte antibody for the analyte capture reagent is less than about 25% (e.g., about 10%, about 5%, about 1%, about 0.1%, about 0.01% or about 0.001%) of the affinity of the antibody for analyte; (c) washing the solid phase to remove unbound conjugate; and (d) measuring the amount of the label associated with the solid phase to determine the presence or amount of the analyte in the sample.

In yet another aspect, the disclosure is directed to a composition including an anti-T4 antibody and an anti-SDMA antibody. At least one of the anti-T4 antibody and the anti-SDMA antibody may be attached to biotin, streptavidin, avidin, or a detectable label. The antibodies may be lyophilized. The composition may be part of a kit includes a vessel containing the composition. The kit may further include a wash solution and may further include an enzyme substrate.

DESCRIPTION OF THE DRAWINGS

The accompanying drawings, which are included to provide a further understanding of the disclosure, are incorporated in and constitute a part of this specification, illustrate embodiments of the disclosure, and together with the detailed description serve to explain the principles of the disclosure. No attempt is made to show structural details of the disclosure in more detail than may be necessary for a fundamental understanding of the disclosure and various ways in which it may be practiced.

DESCRIPTION

Figure 1A:
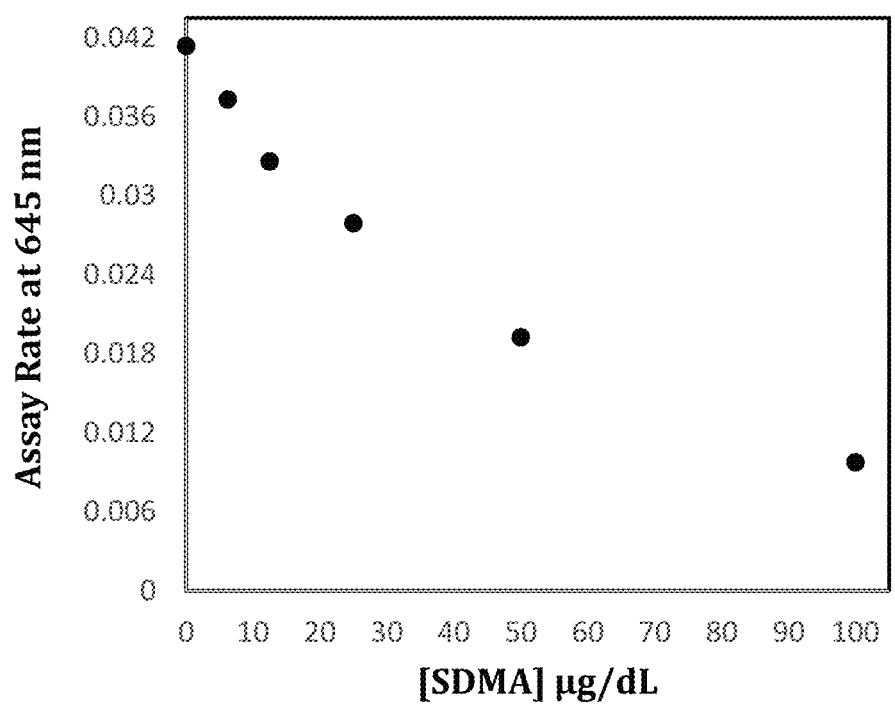
FIGS. 1A and 1B show SDMA calibration curves prepared according to methods of the disclosure using protein G6PDH-MMA passively coated latex particles as solid phase and Anti-SDMA SPDP HRP conjugate.

In various aspects, the disclosure provides devices, reagents, kits and methods for detecting symmetrical dimethyl arginine (SDMA) in sample, such as a biological sample from an animal. The method includes detecting the presence or amount of SDMA in the sample by using an immunoassay format, such as a competitive immunoassay. The assay includes the use of antibodies to SDMA that are specific for SDMA and that have less affinity for other arginine derivatives, including asymmetrical dimethyl arginine (ADMA), L-arginine and N-methylarginine.

Before describing the disclosure in further detail, a number of terms are defined:

Ab is antibody.

The structure of arginine is:

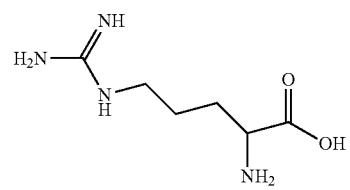 [SMILES: N=C(N)NCCCC(N)C(=O)O]

L-Arginine is the L-isomer of arginine.

Arginine derivatives include, but are not limited to, methylated arginine derivatives, acylated arginine and derivatives, and compounds having the following structure

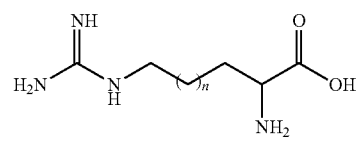

wherein n is an integer 0, 2, or 3. In some embodiments, arginine derivatives do not include SDMA, ADMA, and/or N-MMA for definitional purposes in order to provide a class of arginine derivatives that does not include on or more of SDMA, ADMA and N-MMA.

ADMA is asymmetrical dimethylarginine. The structure of ADMA is:

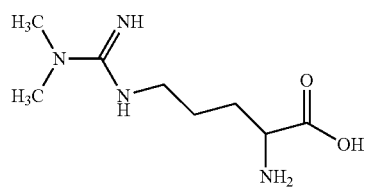

N-MMA is N-monomethylarginine, or simply N-methylarginine, which is also referred to herein as simply "MMA." The structure of N-monomethylarginine is:

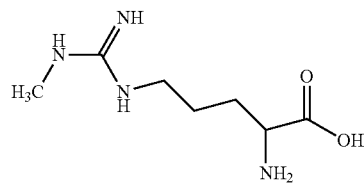

SDMA is symmetrical dimethylarginine. The structure of SDMA is:

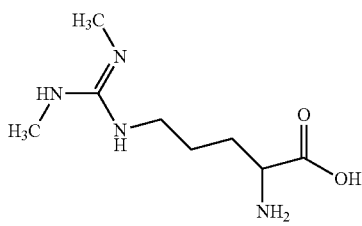

Free SDMA refers to SDMA and SDMA salts that are not part of a polypeptide chain. One or more amino acid residues of SDMA can be present in a polypeptide.

The term "methylated arginine derivative," as used herein, refers to compounds have the following structure:

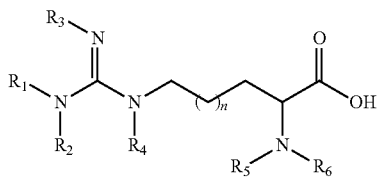

wherein n is an integer 0, 1, 2 or 3; and $R_1$, $R_2$, $R_3$, $R_4$, $R_5$, and $R_6$ are each independently hydrogen or methyl, provided that at least one of $R_1$, $R_2$, $R_3$, $R_4$, $R_5$, and $R_6$ is methyl. Examples of methylated arginine derivatives include MMA, SDMA, and ADMA, although certain subsets of the methylated derivatives, for definitional purposes, do not include one or more of these compounds.

The term "salt," as used herein, means a salt formed between an acid and a basic functional group of a compound. Illustrative salts include, but are not limited, to sulfate, citrate, acetate, oxalate, chloride, bromide, iodide, nitrate, phosphate, a lactate, tartrate, ascorbate, succinate, maleate, fumarate, gluconate, glucaronate, saccharate, formate, benzoate, glutamate, and salts. The term "salt" also refers to a salt formed between a compound having an acidic functional group, such as a carboxylic acid functional group, and an inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines.

The term "analog," as used herein, generally refers to a compound in which one or more individual atoms have been replaced with a different atom(s) or with a different functional group(s) that provide a means to join the analyte to another moiety, such as a label or solid matrix. For example, a means to join the analyte to another moiety may be a linker. An analog may compete with the analyte for a receptor. In particular, the analyte analog can bind to an antibody in a manner similar to the analyte. Because covalent binding of the analyte to a matrix or another molecule is often accomplished through the use of an analyte analog, the disclosure herein of simply "the analyte" attached to or conjugated to a matrix or another molecule includes the use of an analyte analog to accomplish such covalent attachment or conjugation as would be readily understood by one of ordinary skill in the art of immunoassays. For instance, various analogs of MMA are disclosed at in the Examples below.

A "derivative" of the analyte refers to a modified form of the analyte that can compete with the analyte for a receptor, the modification being the addition or modification of a functional group(s) that does not provide a means to join an analyte to a to another moiety such as a label or solid matrix. Two molecules may be derivatives of each other, such that either molecule may be an analyte or a derivative of the analyte as the case may be. For instance, arginine, SDMA, MMA and L-arginine are all derivatives of each other, the difference between the molecules being isomerism, or the presence or location of one or two methyl groups.

The term "antibody," as used herein, generally refers to a glycoprotein produced by B lymphocyte cells in response to exposure to an antigen and binds specifically to that antigen. The term "antibody" is used in its broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

The term "antibody fragment," as used herein, refers to a portion of a full length antibody, generally the antigen binding or variable domain thereof. Specifically, for example, antibody fragments may include Fab, Fab', F(ab')$_2$, and Fv fragments; diabodies; linear antibodies; single-chain antibody molecules; and multispecific antibodies from antibody fragments.

The term "monoclonal antibody," as used herein generally refers to an antibody obtained from a population of substantially homogeneous antibodies, i.e., the individual antibodies including the population are identical. Monoclonal antibodies are highly specific, being directed against a single antigenic site. In contrast to polyclonal antibody preparations, which typically include different antibodies directed against different epitopes, each monoclonal antibody is directed against a single epitope on the antigen. The modifier "monoclonal" merely refers to the character of the antibody and is not to be construed as requiring production of the antibody by any particular method. Specifically, for example, monoclonal antibodies may be made by hybridoma methodologies, or may be made by recombinant DNA methods, or may be isolated from phage antibody libraries using known techniques.

As used herein, an "anti-SDMA antibody," "anti-SDMA antibody portion," or "anti-SDMA antibody fragment" and/ or "anti-SDMA antibody variant" and the like include any protein or peptide containing molecule that includes at least a portion of an immunoglobulin molecule, such as, but not limited to, one complementarity determining region (CDR) of a heavy chain or light chain constant region, a framework region, or any portion thereof. Anti-SDMA antibodies as used herein may be prepared according to U.S. Pat. No. 8,481,690, which is incorporated herein in its entirety.

The term "antigen," as used herein, generally refers to a substance that is capable, under appropriate conditions, of reacting with an antibody specific for the antigen.

The term "analyte," as used herein, generally refers to the substance, or set of substances in a sample that are detected and/or measured. According to example aspects of the disclosure, SDMA or a salt of SDMA are considered examples of an analyte.

The term "biological sample," as used herein, generally refers to a sample of tissue or fluid from a human or animal including, but not limited to whole blood, plasma, serum, spinal fluid, lymph fluid, abdominal fluid (ascites), the external sections of skin, respiratory, intestinal and genitourinary tracts, tears, saliva, urine, blood cells, tumors, organs, tissue, and sample of in vitro cell culture constituents. Many such samples require processing prior to analysis. Sample includes both raw samples and/or processed samples.

The term "immunoassay," as used herein, generally refers to a test that employs antibody and antigen complexes to generate a measurable response. An "antibody:antigen complex" may be used interchangeably with the term "immunocomplex." Immunoassays, in general, include noncompetitive immunoassays, competitive immunoassays, homogeneous immunoassays, and heterogeneous immunoassays. In "competitive immunoassays," unlabeled analyte (or antigen) in the test sample is measured by its ability to compete with labeled antigen in the immunoassay. The unlabeled antigen blocks the ability of the labeled antigen to bind because the binding site on the antibody is already occupied. In "competitive immunoassays," the amount of antigen present in the test sample is inversely related to the amount of signal generated from the label. Conversely, in "noncompetitive immunoassays," also known as "sandwich" immunoassays, the analyte is bound between two highly specific antibody reagents to form a complex and the amount of antigen is directly proportional to the amount of signal associated with the complex. Immunoassays that require separation of bound antibody:antigen complexes are generally referred to as "heterogeneous immunoassays," and immunoassays that do not require separation of antibody:antigen complexes are generally referred to as "homogeneous immunoassays." One of skill in the art would readily understand the various immunoassay formats.

The term "immune complexes," as used herein, generally refers to the complexes formed by the binding of antigen and antibody molecules, with or without complement fixation. When one of either the antibody or antigen is labeled, the label is associated with the immune complex as a result of the binding between the antigen and antibody. Therefore, when the antibody is labeled, the label becomes associated with the antigen as a result of the binding. Similarly, when the antigen is labeled (e.g., an analyte analog having a label), the label becomes associated with the antibody as a result of the binding between the antigen and the antibody.

The term "label," as used herein, refers to a detectable compound, which can be conjugated directly or indirectly (e.g., via covalent or non-covalent means, alone or encapsulated) to an antibody or analogs of the disclosure. The label may be detectable by itself (e.g., radioisotope labels, chemiluminescent dye, electrochemical labels, metal chelates, latex particles, or fluorescent labels) or, in the case of an enzymatic label, may catalyze chemical alteration of a substrate compound or composition which is detectable (e.g., enzymes such as horseradish peroxidase, alkaline phosphatase, and the like). The label employed in the current disclosure could be, but is not limited to: alkaline phosphatase; glucose-6-phosphate dehydrogenase ("G6PDH"); horse radish peroxidase (HRP); chemiluminescers such as isoluminol, fluorescers such as fluorescein and rhodamine compounds; ribozymes; and dyes. The label may also be a specific binding molecule which itself may be detectable (e.g., biotin, avidin, streptavidin, digoxigenin, maltose, oligohistidine, 2, 4-dinitrobenzene, phenylarsenate, ssDNA, dsDNA, and the like). The utilization of a label produces a signal that may be detected by means such as detection of electromagnetic radiation or direct visualization, and that can optionally be measured.

The term "polypeptide," as used herein, generally refers to a molecule having a sequence of amino acids linked by peptide bonds. This term includes proteins, fusion proteins, oligopeptides, cyclic peptides, and polypeptide derivatives. Antibodies and antibody derivatives are discussed above in a separate section, but antibodies and antibody derivatives are, for purposes of the disclosure, treated as a subclass of the polypeptides and polypeptide derivatives.

The terms "solid support", "solid phase" and "solid matrix" as used herein, refer to a non-aqueous matrix to which the binding partner of the present disclosure can adhere. Examples of solid supports, solid phases, and solid matrices include supports formed partially or entirely of glass (e.g., controlled pore glass), synthetic and natural polymers, polysaccharides (e.g., agarose), polyacrylamides, polystyrene, polyvinyl alcohols and silicones, chromatographic strips, microtiter polystyrene plates, or any other substances that will allow bound binding partners to be washed or separated from unbound materials. In some embodiments, the solid supports, phases and matrices can be porous. In certain embodiments, depending on the application, the solid support, solid phase and solid matrix can be the well of an assay plate. The solid support, solid phase and solid matrix may include an analytical test slide as described in US Patent Publication No. 2014/0315216, which is incorporated herein by reference in its entirety.

The term "particle" or "particles" in connection with the disclosure include, for example, particles of latex, polystyrene, or of other support materials such as silica, agarose, ceramics, glass, polyacrylamides, polymethyl methacrylates, carboxylate modified latex, melamine, and Sepharose. The particles will vary in size from about 0.1 microns to about 100 microns, for example about 0.1, 0.5, 1.0, 5, 10, 20, 30, 40 50, 60, 70, 80 90 or 100 microns. In particular, useful commercially available materials include carboxylate modified latex, cyanogen bromide activated Sepharose beads, fused silica particles, isothiocyanate glass, polystyrene, and carboxylate monodisperse microspheres. The particles may be magnetic or paramagnetic. Particles suitable for use in the present invention are capable of attachment to other substances such as derivatives, linker molecules or proteins. The capability of the particles to be attached to other substances can result from the particle material as well as from any surface modifications or functional groups added to the particle. The particles can be functionalized or be capable of becoming functionalized in order to covalently or non-covalently attach proteins, linker molecules or derivatives as described herein. Suitable functional groups include, for example, amine, biotin, streptavidin, avidin, protein A, sulfhydryl, hydroxyl and carboxyl.

"Receptor" refers to any compound or composition capable of recognizing a particular spatial and polar organization of a molecule, e.g., epitopic or determinant site. Illustrative receptors include antibodies, Fab fragments, and the like.

The term "cross-reactivity," as used herein, generally refers to the ability of an individual antigen binding site of an antibody to react with more than one antigenic determinant or the ability of a population of antibody molecules to react with more than one antigen. In general, cross reactions arise because (i) the cross reacting antigen shares an epitope in common with the immunizing antigen or (ii) it has an epitope which is structurally similar to one on the immunizing antigen (multispecificity).

"Binding specificity" or "specific binding" refers to the substantial recognition of a first molecule for a second molecule, for example a polypeptide and a polyclonal or monoclonal antibody, or an antibody fragment (e.g. a Fv, single chain Fv, Fab', or F(ab')2 fragment) specific for the polypeptide. For example, "specificity," as used herein, generally refers to the ability of an individual antibody combining site to react with only one antigenic determinant or the ability of a population of antibody molecules to react with only one antigen. In general, there is a high degree of specificity in antigen-antibody reactions. Antibodies can distinguish differences in (i) the primary structure of an antigen, (ii) isomeric forms of an antigen, and (iii) secondary and tertiary structure of an antigen. Antibody-antigen reactions that exhibit high specificity exhibit low cross reactivity.

"Substantial binding" or "substantially bind" refers to an amount of specific binding or recognizing between molecules in an assay mixture under particular assay conditions. In its broadest aspect, substantial binding relates to the difference between a first molecule's incapability of binding or recognizing a second molecule, and the first molecules capability of binding or recognizing a third molecule, such that the difference is sufficient to allow a meaningful assay to be conducted distinguishing specific binding under a particular set of assay conditions, which includes the relative concentrations of the molecules, and the time and temperature of an incubation.

In another aspect, one molecule is substantially incapable of binding or recognizing another molecule in a cross-reactivity sense where the first molecule exhibits a reactivity for a second molecule that is less than 25%, less than 10%, less than 5% or less than 1% of the reactivity exhibited toward a third molecule under a particular set of assay conditions. Specific binding can be tested using a number of widely known methods, e.g., an immunohistochemical assay, an enzyme-linked immunosorbent assay (ELISA), a radioimmunoassay (RIA), or a western blot assay.

Affinity for an antibody to its target can be influenced by the environment of the antibody and/or target. For example, when one or the other is bound to a solid phase or conjugated to another molecule, the affinity between the molecules may be different than between the two molecules in solution. In certain embodiments, the methods of the disclosure herein exploit the differences in affinity of an anti-analyte antibody for the analyte when the analyte is in solution versus the affinity when the analyte is bound to a solid phase. In addition, in various embodiments, the methods of the disclosure exploit the differences of an antibody's affinity for the analyte versus the antibodies affinity for derivatives of the analyte. For instance, while an anti-analyte antibody may not substantially bind a derivative of the analyte, the antibody may bind the derivative with sufficient reactivity such that even low binding affinity of the antibody and derivative can be useful in the methods of the disclosure. For example, low binding affinity (e.g., the anti-analyte antibody binds the derivative of the analyte with less than 25% of the reactivity of the binding of the antibody to the analyte), can use useful when the antibody and analyte are in solution and the derivative is bound to a solid phase.

Turning now to the various aspects of the disclosure, the disclosure is directed to an immunological method, devices, reagents, and kits for detecting the presence of an amount of free SDMA in a biological sample. The method may include controls, calibrators or standards including one or more of SDMA or SDMA analogs. In particular, the method may be accomplished using immunoassay techniques well known to those of skill in the art, including, but not limited to, using microplates, porous matrices, flow through solid phase matrices, and lateral flow devices. Animal subjects from which samples are obtained for detecting SDMA, include human and non-human animals (e.g., companion animals, livestock, etc.) subjects. The determination of disease states associated with the presence or amount of SDMA can be conducted for both human and non-human subjects.

In a particular aspect, an example device of the disclosure includes a solid matrix that has a particle non-diffusively bound thereto, wherein the particle includes a capture reagent covalently or passively (non-covalently) bound thereto. The capture reagent includes the analyte or a derivative of the analyte covalently attached to a protein that is attached to a particle. The matrix may be porous matrix, which can be arranged in a cartridge or housing for ease of handling and for use on automated analyzers. See US Patent Publication No. 2014/0315216.

When the analyte is SDMA, the derivative includes arginine derivatives, such asymmetrical dimethylarginine (ADMA), L-arginine, N-methylarginine (MMA), acylated ADMA, acylated L-arginine, acylated MMA, and compounds having the following formula:

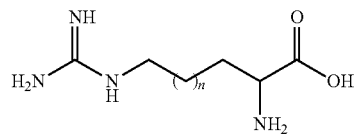

wherein n is an integer 0, 1, 2, or 3. The asymmetrical dimethylarginine (ADMA), L-arginine, N-methylarginine (MMA), acylated ADMA, acylated L-arginine, and acylated MMA may be further derivatized. In one aspect, the arginine derivatives have an affinity for an anti-SDMA antibody or an anti-acyl-SDMA antibody when the derivatives are immobilized on a solid support. The arginine derivative may itself be SDMA or acyl-SDMA. Or in some embodiments, one or more of SDMA, ADMA N-MMA and their acylated forms are specifically excluded from the group of arginine derivatives.

A variety of proteins can be used for attachment of analyte or derivative of the analyte to solid phase. Particular examples include Bovine Serum Albumin (BSA), ovalbumin, Keyhole Limpet Hemocyanin (KLH), and Glucose-6-Phosphate Dehydrogenase (G6PDH). While G6PDH is well known as an enzymatic label, in this context it functions to attach the analyte or derivative to the solid phase. It does not function as a label unless the appropriate substrate is used, which can be avoided in the method of the disclosure by using a molecule other than G6PDH (such as HRP) as a label in the assay as further described herein. G6PDH may be derived from a eukaryote, a prokaryote, a yeast or recombinant expression.

Any recitations of a protein to which an analyte derivative or analog is bound, such as BSA, KLH, ovalbumin, or G6PDH, also include variants, isoforms, fragments and mutants of the protein. The variants, isoforms, fragments and mutants retain the ability to bind or to be conjugated to the analyte, analog or derivative and/or to bind to a solid support. If the protein is an enzyme, the variants, isoforms, fragments or mutants of the protein may or may not retain the enzymatic activity. For example, mutant forms of G6PDH having various amino acid substitutions are described in U.S. Pat. No. 6,455,288, which is incorporated by reference herein in its entirety.

When the protein is not covalently attached to the particle, the non-covalent attachment of the protein may be more tolerant to surfactants or high salt concentrations than the non-covalent attachment of BSA, ovalbumin or KLH to the particle. For example, the non-covalent attachment of G6PDH is more tolerant to surfactants and high salt concentration to polystyrene particles than the attachment of BSA, ovalbumin or KLH. The tolerance of the attachment of the proteins to the particles under various reaction conditions may be tested according to methods well known to those of skill the art. The solid phase assay format is a commonly used binding assay technique. There are a number of assay devices and procedures wherein the presence of an analyte is indicated by the analyte's binding to a conjugate and/or an immobilized complementary binding member. In one particular aspect, an immobilized binding member (e.g., an arginine derivative or analog thereof) is bound, or becomes bound during the assay, to a solid phase such as a reaction well, dipstick, test strip, flow-through pad, paper, fiber matrix or other suitable solid phase material. The binding reaction between free SDMA in the sample and an anti-SDMA antibody is determined by combining the sample with an amount of the antibody that is conjugated to a label. After contacting the mixture of the sample and the conjugate to the solid phase, the mixture and solid phase are incubated to allow for binding between the immobilized arginine derivative or analog thereof and the anti-SDMA antibody. Following the incubation, unbound reactants are removed from the solid phase. The amount of the label that becomes associated with the solid phase through binding of the antibody to the derivative or analog is measured. The amount of the label associated with the solid phase is inversely proportional to the amount of free SDMA in the sample.

Immobilization of an arginine derivative or analogs thereof onto a device or solid support is performed so that the derivative or analog will not be washed away by the sample, diluent and/or wash procedures.

In another aspect, the disclosure includes one or more labeled antibodies that can be mixed with a test sample prior to application of the mixture to a solid support. In this case, an arginine derivative or analog thereof can be attached to the solid support so that the analog will not be washed away by the sample, diluent and/or wash procedures. Labeled antibodies in the sample bind to SDMA in the sample and are, therefore, not available for binding with the analogs on the solid support. After application of the mixture to the solid support, and an appropriate incubation, the mixture is washed from the solid support. Antibodies that have not bound to sample SDMA will become bound to the arginine derivative or analog thereof on the solid support. The presence or amount of SDMA in the sample is inversely proportional to the amount of antibody that has become bound to the SDMA analog. The signal associated with the label on the antibody can be measured by the appropriate method. An example analyzer for use in measuring the label is the CATALYST DX® system (IDEXX Laboratories, Inc.), which can be combined with a single layer solid phase in a cartridge or housing that mounts in the analyzer as described in US Patent Publication No. 2014/0315216.

More particularly, an example of the method of the disclosure includes forming a mixture including the sample and a labeled conjugate including an anti-SDMA antibody conjugated to a label. Anti-SDMA antibodies and the conjugation of labels to the antibodies are described, for example, in U.S. Pat. No. 8,481,690. The mixture is contacted with a device of the disclosure that includes a solid matrix that has a particle non-diffusively bound thereto, wherein the particle includes a capture reagent covalently or passively (non-covalently) bound thereto. As described herein, the capture reagent includes SDMA or derivative therefore (e.g., arginine derivatives) covalently attached to a protein that is attached to a particle. The solid support is washed to remove conjugate that is not bound to the solid support. The amount of the label associated with the solid support is measured to determine the presence or amount of SDMA in the sample.

As described herein, SDMA itself may be bound to the solid phase through the conjugation to a protein and the attachment of the protein to the particle. Examples of conjugates of SDMA to proteins are shown in US Patent Application Publication No. US2016/0245801, which incorporated herein in its entirety. In other embodiments, derivatives of SDMA (e.g., arginine derivatives, methylated arginine derivatives) can be used in place of SDMA, wherein the anti-SDMA antibody has less affinity for the derivative than the affinity for SDMA. In particular examples, the affinity of the anti-SDMA antibody for the derivative is less than about 25%, less than 10%, less than 5%, less than 1%, less than 0.1%, less than 0.01% or less than 0.001% of the affinity of the antibody for SDMA.

The matrix material includes fibrous mats composed of synthetic or natural fibers (e.g., glass or cellulose-based materials or thermoplastic polymers, such as, polyethylene, polypropylene, or polyester); sintered structures composed of particulate materials (e.g., glass or various thermoplastic polymers); or cast membrane films composed of nitrocellulose, nylon, polysulfone or the like (generally synthetic in nature). The matrix may also be composed of sintered, fine particles of polyethylene, commonly known as porous polyethylene, such as sintered polyethylene beads. Such material can have a density of between 0.35 and 0.55 grams per cubic centimeter, a pore size of between 5 and 40 microns, and a void volume of between 40 and 60 percent. Particulate polyethylene composed of cross-linked or ultra high molecular weight polyethylene may also be used. An example matrices includes 10-15 micron porous polyethylene from Chromex Corporation FN #38-244-1 (Brooklyn, N.Y.) and FUSION 5™ matrix available from Whatman, Inc., USA.

The use of reagent-impregnated test strips in specific binding assays is also well-known. In such procedures, a test sample is applied to one portion of the test strip and is allowed to migrate or wick through the strip material. Thus, the analyte to be detected or measured passes through or along the material, possibly with the aid of an eluting solvent which can be the test sample itself or a separately added solution. The analyte migrates into a capture or detection zone on the test strip, wherein an analyte analog or other compound capable of binding an anti-analyte antibody is immobilized. The extent to which the antibody becomes bound in the detection zone can be determined with the aid of a label conjugated to the antibody, wherein the conjugate is mixed with the sample. In one embodiment, an analog that is capable of binding the antibody is immobilized on a solid support at a distinct location. Following addition of the sample-conjugate mixture, detection of SDMA-antibody complexes on the solid support can be by any means known in the art. For example, U.S. Pat. No. 5,726,010, which is incorporated herein by reference in its entirety, describes an example of a lateral flow device, the SNAP® immunoassay device (IDEXX Laboratories), useful in the present disclosure.

Other detection technologies employ magnetic particles or microbeads independent of the particle used for the capture reagent as described herein. For example, superparamagnetic iron oxide impregnated polymer beads can be associated with, for example, the analyte or the derivative for the analyte through the use of the particle as part of the capture reagent. The beads used for the solid phase can be isolated or separated out of solution magnetically. Once isolation has occurred, other testing may be conducted, including observing the labels, whether directly optically or by means of a camera.

In a further aspect, the disclosure relates to capture reagents using arginine derivatives and analogs thereof for use in methods for determining SDMA according to the disclosure herein. In particular, the disclosure relates to thiol-containing, hydroxyl-containing, amino containing, and carboxylate containing analogs of arginine derivatives, where the thiol group, hydroxyl group, amino group, or carboxylate group enables the derivative to be linked to another molecule (conjugation target), such as an activated protein, to form a conjugate. The analogs of the disclosure enable the derivatives to be linked to a conjugation target such as a protein, polypeptide, detectable label, solid support, and the like.

On aspect of the disclosure relates to a capture reagent including an analog of an arginine derivative including a methylated arginine derivative, for example N-methylarginine (MMA) or acylated MMA, attached to a particle. In one embodiment, the analog is bound to the particle through a linker such that the analog is covalently attached to a protein that is attached to a particle. The protein may be either covalently or non-covalently (passively) attached to the particle. The protein may be at least one of Bovine Serum Albumin (BSA), ovalbumin, Keyhole Limpet Hemocyanin (KLH), and Glucose-6-Phosphate Dehydrogenase (G6PDH). Attachment of the analog to the particle, either passively or covalently, and using the particle to anchor the analog to the solid phase results in increased linear range of the assay as compared to the use of a solid phase with the analog directly attached thereto. This embodiment also results in the reduction or elimination of sample bias as further described and exemplified herein.

In one example of the capture reagent of the disclosure, the linker includes the following structure:

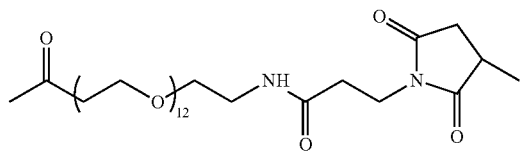

When MMA is attached to a particle with this linker the capture reagent has the following structure:

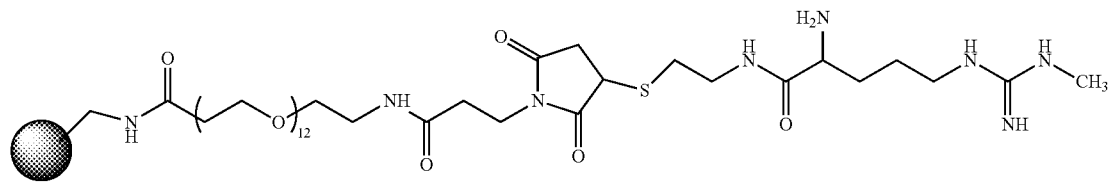

In addition, the following MMA analogs may have the following structures to provide or linkage and attachment to proteins for use, for example in capture reagents:

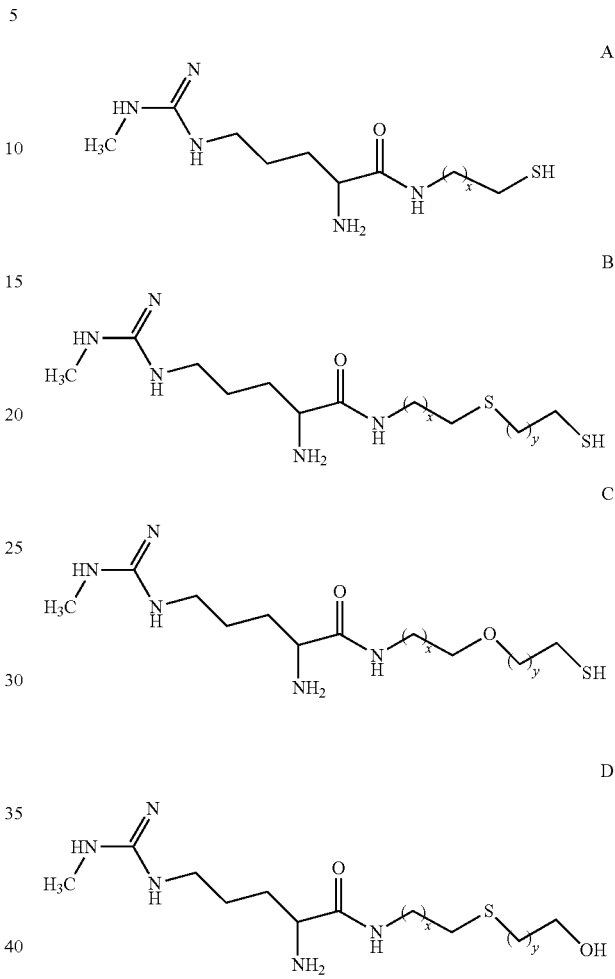

wherein x and y are integers ranging from 1 to 5.

According to one embodiment, the MMA analogs of the disclosure have the following general formula:

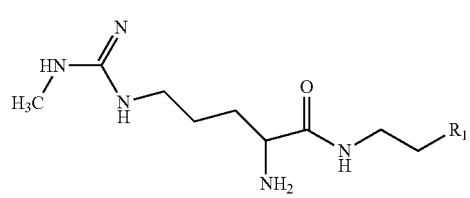

where $R_1$ may be a thiol (or protected thiol), a hydroxyl (or protected hydroxyl), an amino (or protected amino) group, or a carboxylate (including carboxylic acid) or protected carboxylate group.

Suitable thiol, hydroxyl, amino, and carboxylate protecting groups are known to those skilled in the art such as those described, for example, in T. W. Greene, et al. *Protective Groups in Organic Synthesis,* 3rd ed. (1999).

In one particular embodiment, the disclosure is directed to an MMA analog of formula (1):

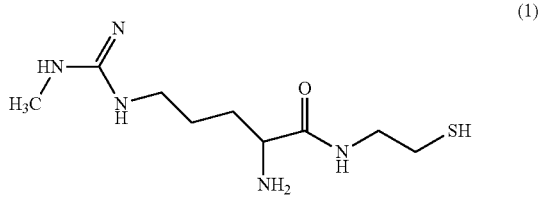 [SMILES: CNC(=N)NCCCC(N)C(=O)NCCS]

(1)

or a salt thereof. The compound of formula (1) provides an available thiol that can react with a conjugation target that includes an appropriate "thiol-reactive site," i.e., a site that will react with a thiol group. For example, maleimides, alkyl and aryl halides, and alpha-haloacyls are illustrative thiol-reactive sites that can react with thiols to form thio-ethers. Similarly, pyridyl disulfides can react with thiols to form mixed disulfides.

In another embodiment, $R_1$ is X—$R_2$, wherein X is —S—, —O—, —N—, or, —COO— and $R_2$ is a label having a thiol, hydroxyl, amino, or carboxylate reactive group.

In one embodiment, $R_1$ is X—$R_2$, wherein X is —S—, —O—, —N—, or, —COO— and $R_2$ is a protein that has been functionalized to include a thiol, hydroxyl, amino, or carboxylate reactive group.

In one embodiment, the MMA analog is conjugated to a maleimide activated protein, such as, for example, maleimide activated keyhole limpet protein (KLH) or maleimide activated bovine serum albumin (BSA).

In one embodiment, the compound of formula (1) is conjugated to a maleimide activated protein, such as, for example, maleimide activated keyhole limpet protein (KLH) or maleimide activated bovine serum albumin (BSA).

Thus, in a specific embodiment, the disclosure relates to a conjugate of a compound of formula (1) and maleimide activated protein having the formula:

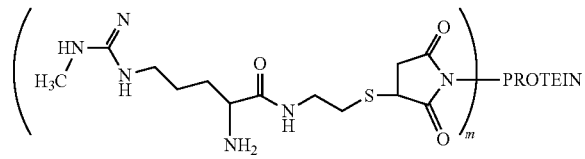

Typically, m is greater than 5. However, the value for m is variable. For example, m is about 15 maleimide groups per protein in maleimide activated BSA commercially available from Sigma-Aldrich of St. Louis, Mo.; m is about 80 maleimide groups per protein in maleimide activated KLH commercially available from Sigma-Aldrich; m is in a range of about 15 to about 25 maleimide groups per protein in maleimide activated BSA commercially available from Thermo Scientific Pierce Protein Research Products of Rockford, Ill.; m is greater than about 400 maleimide groups per protein in maleimide activated KLH commercially available from Thermo Scientific Pierce Protein Research Products; and m is in a range of about 150 to about 300 maleimide groups per protein in maleimide activated KLH commercially available from A. G. Scientific of San Diego, Calif. In general, m is limited by the number of available amine groups present in an immunogenic protein. The number of available amines can be increased by conjugating the immunogenic protein to polyamines.

In one embodiment, PROTEIN is BSA and m is greater than about 5. In one embodiment, PROTEIN is BSA and m is greater than about 10. In one embodiment, PROTEIN is BSA and m is greater than about 25. In one embodiment, PROTEIN is BSA and m is greater than about 50. In one embodiment, PROTEIN is BSA and m is greater than about 75. In one embodiment, PROTEIN is BSA and m is in a range of about 5 to about 80. In one embodiment, PROTEIN is BSA and m is greater than about 75. In one embodiment, PROTEIN is BSA and m is in a range of about 10 to about 80. In one embodiment, PROTEIN is BSA and m is greater than about 75. In one embodiment, PROTEIN is BSA and m is in a range of about 20 to about 80. In one embodiment, PROTEIN is BSA and m is greater than about 75. In one embodiment, PROTEIN is BSA and m is in a range of about 30 to about 80.

In one embodiment, PROTEIN is KLH and m is greater than about 5. In one embodiment, PROTEIN is KLH and m is greater than about 50. In one embodiment, PROTEIN is KLH and m is greater than about 100. In one embodiment, PROTEIN is KLH and m is greater than about 200. In one embodiment, PROTEIN is KLH and m is greater than about 300. In one embodiment, PROTEIN is KLH and m is greater than about 400. In one embodiment, PROTEIN is KLH and m is greater than about 500. In one embodiment, PROTEIN is KLH and m is greater than about 600. In one embodiment, PROTEIN is KLH and m is greater than about 700. In one embodiment, PROTEIN is KLH and m is greater than about 800. In one embodiment, PROTEIN is KLH and m is in a range of about 5 to about 800. In one embodiment, PROTEIN is KLH and m in a range of about 5 to about 600. In one embodiment, PROTEIN is KLH and m in a range of about 5 to about 400. In one embodiment, PROTEIN is KLH and m in a range of about 5 to about 200. In one embodiment, PROTEIN is KLH and m in a range of about 5 to about 100. In one embodiment, PROTEIN is KLH and m in a range of about 100 to about 200. In one embodiment, PROTEIN is KLH and m ranges in a range of 100 to about 300. In one embodiment, PROTEIN is KLH and m in a range of about 100 to about 400. In various aspects, PROTEIN is KLH and m in a range of about 100 to about 500, about 100 to about 600, about 100 to about 700, about 100 to about 800, or about 100 to about 1,000.

The conjugate of a compound of formula (1) and maleimide activated protein can be characterized using methods well known to those skilled in the art (see, for example, Sigma-Aldrich Technical Bulletin for Maleimide Activated BSA, KLH Conjugation Kit (catalog no. MBK1)).

In an alternate embodiment, the MMA analog is linked directly to a solid support through the thiol, hydroxyl, amino, or carboxylate group.

The label may be detectable by itself (e.g., radioisotope labels, chemiluminescent dye, electrochemical labels, metal chelates, latex particles, or fluorescent labels) or, in the case of an enzymatic label, may catalyze chemical alteration of a substrate compound or composition which is detectable (e.g., enzymes such as horseradish peroxidase, alkaline phosphatase, and the like). The label may be a specific binding molecule which itself may be detectable (e.g., biotin, avidin, streptavidin, digoxigenin, maltose, oligohistidine, 2, 4-dinitrobenzene, phenylarsenate, ssDNA, dsDNA, etc.). The MMA can be linked to a detectable label using methods well known to those skilled in the art. As an illustrative example, the MMA analog can be linked to maleimide activated peroxidase, from horseradish lyophilized powder (commercially available from Sigma-Aldrich St. Louis, Mo. (catalog no. P1709) following the directions in the product manual).

The analog of formula (1) may be prepared from MMA (commercially available from EMD Chemicals Inc. of Gibbstown, N.J.) according to the following procedure. The primary and secondary amino groups of MMA are protected by reacting MMA with di-tert-butyldicarbonate ($Boc_2O$). The resulting tert-butoxycarbonyl (BOC) protected MMA (($Boc_3$)-MMA, is then linked to a resin. For example, the ($Boc_3$)-MMA can be linked to a cysteamine-4-methoxy trityl resin (commercially available from EMD Chemicals, Inc. of Gibbstown, N.J.) by contacting the ($Boc_3$)-MMA with the resin in the presence of 2-(1H-7-azabenzotriazol-1-yl)-1,1,3,3-tetramethyl uranium hexafluorophosphate methanaminium (HATU) and N,N-diisopropylethylamine (DIPEA) in dimethyl formamide (DMF) to provide resin bound ($Boc_3$)-MMA cysteamide. The BOC protecting groups on the resin bound ($Boc_3$)-MMA cysteamide are removed and the resulting resin bound MMA cystamide cleaved from the resin using, for example, trifluoroacetic acid in dichloromethane, to provide MMA cysteamide, which was converted to the hydrochloride salt by reaction with hydrochloric acid.

The analogs of formula A-D, described above, can be made using similar methodologies.

Using the MMA conjugates or conjugates of other methylated arginine derivatives as described herein, solid phase components of the devices can be constructed. For example, the solid phases may include an analog of MMA or acylated MMA covalently attached to G6PDH that is non-covalently attached a particle that is non-diffusively bound to a solid phase, such as, for example, a porous matrix. As described herein the solid phase can be mounted in a housing or bracket in order to facilitate its use on automated analyzers or in lateral flow devices.

In one aspect, the solid phase including the non-diffusively bound particles can be prepared by spotting a particle spotting diluent containing the particles on the solid phase. For example, a particle spotting diluent can include various buffers, surfactants, and/or other compounds (e.g., sugars) that facilitate adhesion of the particles to the solid phase. The volume of the diluent applied to the solid phase and the concentration of the particles in the diluent will impact the number particles that become bound to the solid phase after the diluent has been applied. In various embodiments, the diluent has a particle concentration of about 0.001% and 1.0%, for instance 0.001%, 0.005%, 0.01%, 0.05%, 0.1%, 0.5%, and 1.0%, including all of the value in between 0.001% and 1.0% as if there were exhaustively enumerated herein.

In use, the solid phase also includes an anti-SDMA antibody bound to the analog, wherein the antibody has less affinity for the analog than it has for SDMA. For instance, the affinity of the anti-SDMA antibody for the analog may be less than about 25%, less than about 10%, less than about 5%, less than about 1%, less than 0.1%, less than 0.01%, or less than 0.001% of the affinity of the antibody for SDMA of the affinity of the antibody for SDMA. In embodiments, the SDMA antibody is labeled.

Similarly, the disclosure is directed to a composition including an analog of N-methylarginine (MMA), acylated MMA, ADMA, acylated ADMA, or another methylated arginine derivative, wherein the analog is complexed with an anti-SDMA antibody. In various embodiments, the antibody has less affinity for the immobilized analog than it has for SDMA in solution. For example, the affinity of the anti-SDMA antibody for the immobilized analog is less than about 25% of the affinity of the antibody for SDMA in solution. In embodiments, the SDMA antibody is labeled. The analog may be covalently attached to a protein, such as Bovine Serum Albumin (BSA), ovalbumin, Keyhole Limpet Hemocyanin (KLH), and Glucose-6-Phosphate Dehydrogenase (G6PDH), and the protein may be non-covalently attached to a solid support. In one embodiment, the protein is non-covalently attached to a particle, which is non-diffusively bound to the solid support. In another embodiment, the protein is covalently attached to the particle through the use, for example, of techniques well known to those of skill in the art.

Anti-SDMA antibodies can be linked to a label to provide detectable anti-SDMA antibodies for use in receptor binding assays, such as immunoassays for SDMA. The anti-SDMA-antibodies can be linked to a label using methods well known to those skilled in the art. E.g., Immunochemical Protocols; Methods in Molecular Biology, Vol. 295, edited by R. Burns (2005)). The detectable anti-SDMA antibodies may be used in various homogenous, sandwich, competitive, or non-competitive assay formats, to generate a signal that is related to the presence or amount of an SDMA in a test sample. In one embodiment, the methods of the disclosure use the ability of the anti-SDMA antibodies specifically bind to free SDMA (i.e., SDMA not part of a polypeptide chain) while also cross-reacting with SDMA derivatives such as ADMA, L-arginine and/or N-methylarginine. In the various embodiments of the methods of the disclosure, the affinity of the anti-SDMA antibody for the derivative is less than about 25%, less than 10%, less than 5%, or less than 1%, less than 0.1%, less than 0.01%, or less than 0.001% of the affinity of the antibody for SDMA.

The disclosure further provides diagnostic kits containing the device and reagents for use in detecting SDMA as described herein. Typically, such a kit contains at least one arginine derivative other than SDMA, such as an SDMA derivative, associated with a solid phase and one reagent that substantially binds to SDMA, such as an anti-SDMA antibody. Kits typically also includes directions or instructions describing how to perform the above-described diagnostic assays, and/or how to interpret the results thereby obtained. Accordingly, in various embodiments, the disclosure is directed to a kit for determining SDMA in a sample. The kit includes the device as described herein that includes a solid phase having immobilized thereon a capture reagent and also includes a conjugate including an anti-SDMA antibody conjugated to a label, wherein the affinity of the anti-SDMA antibody for the capture reagent is less than about 25% of the affinity of the antibody for SDMA. In one embodiment, the kit includes a solid support with the capture reagent including an analog of MMA or acyl MMA, and a conjugate of an anti-SDMA antibody conjugated to a label, wherein the affinity of the anti-SDMA antibody for the capture reagent is less than about 25% of the affinity of the antibody for SDMA.

In one particular example, such a kit would include a device complete with specific binding reagents (e.g., a non-immobilized labeled specific binding reagent and an immobilized analyte capture reagent) and wash reagent, as well as detector reagent and positive and negative control reagents, if desired or appropriate. In addition, other additives can be included, such as stabilizers, buffers, and the like. The relative amounts of the various reagents can be varied, to provide for concentrations in solution of the reagents that substantially optimize the sensitivity of the assay. Particularly, the reagents can be provided as dry powders, usually lyophilized, which on dissolution will provide for a reagent solution having the appropriate concentrations for combining with a sample.

The device may also include a liquid reagent that transports unbound material (e.g., unreacted fluid sample and unbound specific binding reagents) away from the reaction zone (solid phase). A liquid reagent can be a wash reagent and serve only to remove unbound material from the reaction zone, or it can include a detector reagent and serve to both remove unbound material and facilitate analyte detection. For example, in the case of a specific binding reagent conjugated to an enzyme, the detector reagent includes a substrate that produces a detectable signal upon reaction with the enzyme-antibody conjugate at the reactive zone. In the case of a labeled specific binding reagent conjugated to a radioactive, fluorescent, or light-absorbing molecule, the detector reagent acts merely as a wash solution facilitating detection of complex formation at the reactive zone by washing away unbound labeled reagent.

Two or more liquid reagents can be present in a device, for example, a device can include a liquid reagent that acts as a wash reagent and a liquid reagent that acts as a detector reagent and facilitates analyte detection.

The kits and devices of the disclosure can be used in method to reduce assay bias between serum and plasma samples. As described in the examples below, use of a protein to attach analogs of the analyte or derivatives of the analyte to a particle that is then immobilized on a solid phase reduces bias between the samples when compared to analogs that are linked directly to a solid phase (for instance through a linker). Accordingly, in one embodiment, the disclosure is directed a method of reducing or eliminating serum-plasma bias in an immunoassay for an analyte in serum or plasma sample. The method includes forming a mixture of the sample and a labeled conjugate of an anti-analyte antibody conjugated to a label. The mixture is contacted with a device including a solid support having a particle non-diffusively bound thereto, wherein the particle includes a capture reagent including an analog of the analyte or a derivative of the analyte covalently attached to a protein that is attached to the particle. The affinity of the anti-analyte antibody for the analyte capture reagent is less than about 25% (e.g., about 10%, about 5%, about 1%, about 0.1%, about 0.01% or about 0.001%) of the affinity of the antibody for analyte. The method further includes washing the solid phase to remove unbound conjugate and measuring the amount of the label associated with the solid phase to determine the presence or amount of the analyte in the sample.

In a particular example, the disclosure includes a method of reducing or eliminating serum-plasma bias in an immunoassay for symmetrical dimethyl arginine (SDMA) in a serum sample or plasma sample. The method includes forming a mixture including the sample and a labeled conjugate including an anti-SDMA antibody conjugated to a label. The mixture is contacted with a solid support including solid phase of having an analog attached to a protein wherein the protein is non-covalently attached to the particle that is non-diffusively bound to the solid phase. As described more fully herein, the affinity of the anti-SDMA antibody for the arginine derivative is less than about 25% (e.g., about 10%, about 5%, about 1%, about 0.1%, about 0.01% or about 0.001%) of the affinity of the antibody for SDMA. The method includes washing the solid support to remove conjugate that is not bound to the solid support and measuring the amount of the label associated with the solid support to determine the presence or amount of the SDMA in the sample.

As has been described previously, the detection of free SDMA in a biological sample from an animal can provide an indication of renal function in the animal. In addition, an animal may suffer from both hyperthyroidism and kidney disease. Hyperthyroidism can lead to a loss of muscle mass. Creatinine is a poor marker of kidney disease in hyperthyroid patients because decreased muscle mass leads to lower creatinine values. Creatinine is also lowered by the hyperfiltration associated with the increased metabolic state in hyperthyroidism (see Jepson R. Feline hyperthyroidism and chronic kidney disease. In: Proceedings from the BSAVA Congress; Apr. 9-12, 2015; Birmingham, UK). Therefore, hyperthyroidism can mask the presence of kidney disease when creatinine levels are used to monitor kidney function (Williams T. Chronic kidney disease in cats with hyperthyroidism. Clin Brief. Sep. 2015:10-12). SDMA is a superior marker for the detection of kidney disease in hyperthyroid patients because SDMA values are not impacted by muscle mass. For these reasons, it is advantageous for diagnostic purposes to combine an assay for a thyroid marker—such as thyroxine (T4)—with an assay for SDMA. As used herein, an assay for T4 may include an assay for free T4, bound T4 or for total T4. In certain assay configurations, it is advantageous to combine reagents required for T4 and SDMA assays in a single vessel. Combining the reagents in this way reduces complexity, cost and simplifies assay workflows.

Accordingly, in one embodiment, the disclosure is directed to a method of determining the combination of SDMA in a biological sample from a patient. The method includes contacting the sample with an anti-T4 antibody and an anti-SDMA antibody and determining the binding between T4 and the anti-T4 antibody and determining the binding between SDMA and the anti-SDMA antibody. In certain embodiments, either the anti-T4 antibody or the anti-SDMA antibody, or both, are attached to a detectable label. To facilitate the method, an aspect of the disclosure includes a reagent composition including both the anti-T4 and the anti-SDMA antibody. The disclosure is also directed to a kit including a vessel containing the reagent composition, either for storage or for the purposes of conducting assays in combination for T4 and SDMA. In another embodiment, the reagent composition and the components thereof may be lyophilized, which may be in the vessel. The kit may further include a vessel containing a wash solution suitable for both a T4 assay and an SDMA assay. The kit may also include a substrate for an enzymatic label, wherein the label may be attached to the antibodies or that may be conjugated to an analog of SDMA or T4 that is suitable for either a T4 assay and an SDMA assay, depending on the format of the assay.

Without further elaboration, it is believed that one skilled in the art using the preceding description can utilize the disclosure to the fullest extent. Other features and advantages of the disclosure will be apparent from the following Examples. The following are provided for exemplification purposes only and are not intended to limit the scope of the disclosure described in broad terms above. All references cited in this disclosure are incorporated herein by reference.

EXAMPLES

Example 1

Preparation of MMA, ADMA and SDMA Conjugates with G6PDH

Conjugates of MMA, ADMA or SDMA and G6PDH were prepared by conjugating MMA-SH, ADMA-SH or SDMA-SH with G6PDH activated by succinimidyl iodoacetate (SIA). The SIA crosslinker contains an amine-reactive N-hydroxysuccimide (NETS) ester and a sulfhydryl reactive iodoacetyl group. NETS esters react with primary amino groups (—NH2) present on the side chain lysine (K) residues and the N-terminus of glucose-6-phosphate dehydrogenase (G6PDH). After purification by dialysis, the iodoacetyl groups react with the sulfhydryl groups of activated MMA (MMA-SH), ADMA (ADMA-SH) or SDMA (SDMA-SH), resulting in a stable thioether linked G6PDH-MMA or G6PDH-SDMA conjugate. Further details of the conjugation procedures are shown below.

Synthesis of G6PDH-MMA Conjugate

A G6PDH-MMA conjugate has the following structure:

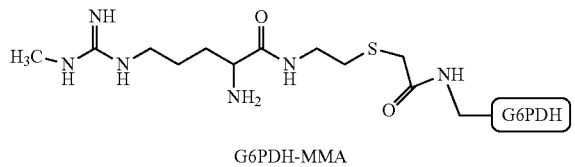 [SMILES: CCNC(=O)CSCCNC(=O)C(N)CCCNC(=N)NC]

G6PDH-MMA

The conjugate was prepared according to the following procedure. First, 108 mg of G6PDH powder was dissolved in 33 ml of MES buffer (50 mM at pH6.5) and incubated 10 min at 25° C. to prepare a 2.11 mg/ml G6PDH stock solution (measured by BCA kit). 28.4 ml of the G6PDH stock solution was added to 9.1 ml of MES buffer (50 mM pH6.5) to form a G6PDH reaction solution. 50 mg of SIA was dissolved in 1 ml DMSO to prepare a SIA stock solution at a concentration of 50 mg/ml. An amount of the 84.9 µl of SIA stock solution (50 mg/ml in DMSO) was added to the aforementioned G6PDH reaction solution (37.5 ml) and was mixed quickly and rotated end-over-end for 2.0 hours at 25° C. The reaction mixture was dialyzed against PBS (4 L) twice at 4° C. and against the MES buffer (50 mM at pH8.0) once at 4° C. EDTA (0.5 M at pH8.0) was then added to the reaction mixture to a final EDTA concentration of 5 mM.

25 mg of MMA-SH.2HCl compound was dissolved in 8.4 ml of 5 mM EDTA solution and mixed well. 5.76 ml of the MMA-SH solution was then added to the above SIA-Activated G6PDH solution and rotated end-over-end at 4 C for 24 hours. The G6PDH-MMA conjugate was then dialyzed at 4° C. three times against PBS and once against the MES buffer (50 mM at pH5.0). The concentration of G6PDH-MMA conjugate was measured by a BCA kit and then stored at −80° C. for further use.

Synthesis of G6PDH-ADMA Conjugate

A G6PDH-ADMA conjugate has the following structure:

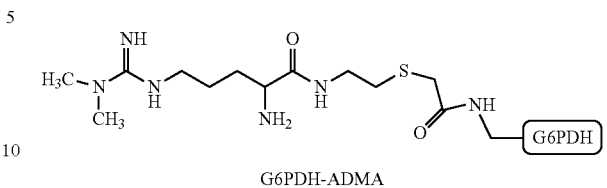

G6PDH-ADMA

The conjugate was prepared according to the following procedure. First, 32.3 mg of G6PDH powder was dissolved in 10 ml of MES buffer (50 mM at pH6.5) and incubated 10 min at 25° C. to prepare a 2.2 mg/ml G6PDH stock solution (measured by BCA kit). 50 mg of SIA was dissolved in 1 ml DMSO to prepare a SIA stock solution at a concentration of 50 mg/ml. An amount of the 18.1 µl of SIA stock solution (50 mg/ml in DMSO) was added to the aforementioned G6PDH reaction solution (8 ml) and was mixed quickly and rotated end-over-end for 2.0 hours at 25° C. The reaction mixture was dialyzed against PBS (4 L) twice at 4° C. and against the MES buffer (50 mM at pH8.0) once at 4° C. EDTA (0.5 M at pH8.0) was then added to the reaction mixture to a final EDTA concentration of 5 mM. 2.7 ml of ADMA-SH synthesized as the following and dissolved in 5 mM EDTA solution (3.8 mM) was then added to the above SIA-Activated G6PDH solution and rotated end-over-end at 4 C for 24 hours. The G6PDH-ADMA conjugate was then dialyzed at 4° C. three times against PBS and once against the MES buffer (50 mM at pH5.0). The concentration of G6PDH-ADMA conjugate was measured by a BCA kit and then stored at −80° C. for further use.

ADMA-SH.2TFA was synthesized according to the following procedure. To a 20 ml vial was added cysteamine 4-methoxytrityl resins (0.9 g, 0.74 mmol), Fmoc-ADMA (pdb)-OH (1.0 g, 1.5 mmol, 2.0 equivalents), HATU (0.7 g, 1.8 mmol, 2.5 equivalents), diisopropyl ethylamine (0.6 mL, 3.7 mmol, 5.0 equivalents) and anhydrous DMF (20 mL). The mixture was capped and rotated end-over-end at 25° C. for 16 hours. The liquid was then removed by filtration and the resins were washed with DMF (20 mL, 4 times) and methanol (20 mL, 4 times). The resins were then treated with 20 ml of 20% piperidine in DMF three times and 30 min incubation for each time. The resins were washed with DMF (20 mL, 4 times) and methanol (20 mL, 4 times), and dried under vacuum. To cleave ADMA-SH from the resins, 3 ml of TFA was added to aforementioned resins and rotated end-over-end for 3 hrs at 25° C. After filtered off the resins, the TFA liquid was evaporated to dry under vacuum and ADMA-SH.2TFA syrup-like product was obtained. The ADMA-SH.2TFA product was dissolved into 5 mM EDTA solution as 3.8 mM ADMA-SH stock measured by Ellman's reagent.

Synthesis of G6PDH-SDMA Conjugate

A G6PDH-SDMA conjugate has the following structure:

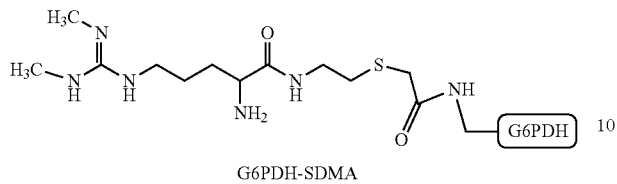

G6PDH-SDMA

The conjugate was prepared according to the following procedure. One vial of Glucose-6-phosphate dehydrogenase (G6PDH) (12 mg) was dissolved in 3 ml MES buffer (50 mM, pH 8.0) and rotated for 1 hour to ensure that the enzyme is fully dissolved in the buffer. The prepared enzyme solution was kept on ice until needed. An additional 4.5 ml of the MES buffer (50 mM, pH 8.0) was added to the enzyme solution, mixed well through vortexing (5 seconds) and kept on ice for 10 minutes. 100 mg of G6P was dissolved in 1 mL deionized water and kept on ice for 10 min. 200 mg of NADH was dissolved in 1 ml deionized water and kept on ice for 10 min. 0.68 ml of the G6P solution and 0.34 ml of the NADH solution were added to the enzyme solution, mixed well through vortexing (5 seconds) and also kept on ice for 10 min. One vial of SIA (50 mg) was dissolved in 0.5 ml DMSO (100 mg/ml), and 0.14 ml of the formed SIA solution was added to the enzyme solution, mixed well through vortexing (5 seconds), covered with aluminum foil, and rotated at room temperature for 2 hours. The solution was then transferred to a G2 Slide-A-Lyzer Dialysis Cassette and dialyzed for five hours against PBS buffer (4 L) at 4° C. in the dark. After changing the dialysis buffer to fresh PBS (4 L), the solution was dialyzed again at 4° C. overnight in the dark. The dialysis buffer was then changed to MES (4 L, 25 mM, pH 8.0) and the solution was dialyzed for 3 hours at 4° C. 12.5 ml of the enzyme solution was removed from the dialysis cassette and 0.32 ml of the MES buffer (1M, pH8.0) and 0.32 ml EDTA (0.2M, pH8.0) was added to bring the final concentration of the solution to 50 mM MES and 5 mM EDTA. If necessary, e.g., if the enzyme solution is less than 12.5 ml, the volumes of MES and EDTA may be adjusted accordingly. The solution was degassed with argon for 5 minutes.

Example 2

Synthesis of KLH-MMA Conjugate

A KLH-MMA conjugate has the following structure:

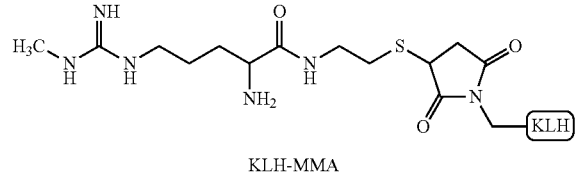 [SMILES: CCN1C(=O)CC(SCCNC(=O)C(N)CCCNC(=N)NC)C1=O]

KLH-MMA

The conjugate was prepared according to the following procedure. 5 mg of maleimide activated-KLH protein was dissolved in 2.0 ml MES buffer (50 mM at pK 8.0) with 5 mM EDTA and then mixed with 2.5 ml of MMA-SH (5 mg/ml in 5 mM EDTA solution). The reaction mixture was rotated end-over-end at 4° C. for over 36 hours and the coupling efficiency was measured. The reaction mixture was then rotated end-over-end for another 24 hours, and the coupling efficiency was measured once again. The prepared KLH-MMA conjugate was then dialyzed with a 10K molecular weight cutoff against PBS (4 L) three times at 4° C. The KLH-MMA conjugate was further dialyzed against a MES buffer (25 mM at pH5.0).

Example 3

Synthesis of KLH-SDMA Conjugate

A KLH-SDMA conjugate has the following structure:

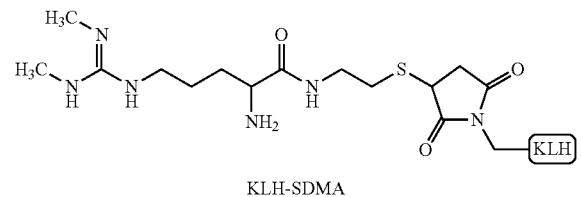 [SMILES: CCN1C(=O)CC(SCCNC(=O)C(N)CCCN/C(=N/C)NC)C1=O]

KLH-SDMA

The conjugate was prepared according to the following procedure. 5 mg maleimide activated-KLH protein was dissolved in 2.0 ml MES buffer (50 mM at pH 8.0) with 5 mM EDTA and then mixed with 2.5 ml of SDMA-SH solution (3.6 mM in 5 mM EDTA). The prepared reaction mixture was rotated end-over-end at 4° C. for over 36 hours, the coupling efficiency was measured, the mixture was then rotated end-of-end for another 24 hours and the coupling efficiency was measured again. The prepared KLH-MMA conjugate was then dialyzed with a 10K molecular weight cutoff against PBS (4 L) three time at 4° C. The conjugate was then dialyzed against a MES buffer (25 mM at pH5.0).

Example 4

Synthesis of BSA-MMA Conjugate

A BSA-MMA conjugate has the following structure:

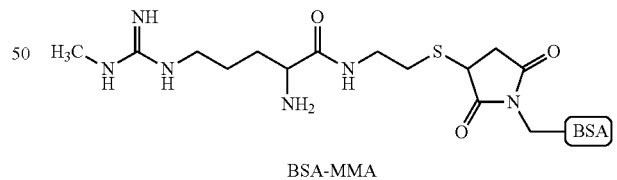

BSA-MMA

The conjugate was prepared according to the following procedure. 25 mg MMA-SH was dissolved into DMSO to make 50 mM MMA-SH stock solution and the concentration was determined via an Ellman's reagent. The MMA-SH stock was diluted into MES buffer (50 mM pH8.0 and 5 mM EDTA) to a final concentration of 3.6 mM. 2.5 ml of the 3.6 mM MMA-SH solution was added into 5 mg of maleimide-activated BSA mixed well and then rotated end-over-end at 4° C. for 36 hours. The prepared BSA-MMA conjugate was then dialyzed against PBS three times (4 L) at 4° C., and against a MES buffer (25 mM at pH5.0) once at 4° C.

Example 5

Synthesis of BSA-SDMA Conjugate

A BSA-SDMA conjugate has the following structure:

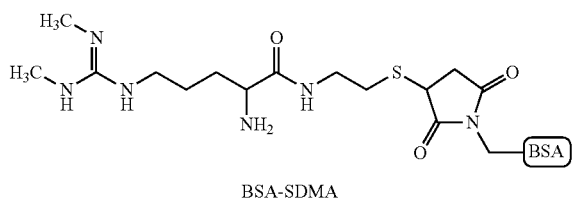

BSA-SDMA

The conjugate was prepared according to the following procedure. SDMA-SH (100 mg) freshly cleaved from SDMA-thiol-resin was dissolved into a MES buffer (50 mM at pH8.0 with 5 mM EDTA) and the concentration of net SDMA-SH was determined via an Ellman's reagent kit to be 3.6 mM. 2.5 ml of SDMA-SH solution was added into 5 mg of maleimide-activated BSA, mixed well and then rotated end-over-end at 4° C. for 36 hours. The prepared BSA-SDMA conjugate was dialyzed against PBS three times (4 L) at 4° C. The conjugate was then dialyzed against a MES buffer (25 mM at pH5.0) once.

Example 6

Passively Coating G6PDH-MMA and G6PDH-ADMA Conjugate on Latex Particles

The following procedure was used to prepare latex particles having passively-coated G6PDH-MMA conjugates. A similar procedure was used to prepare latex particles having passively-coated G6PDH-ADMA conjugates. A similar procedure can be used to passively coat particles with conjugates of G6PDH and other arginine derivatives. In addition, a similar procedure can be used to coat particles with conjugates containing other proteins.

500 μl of a latex particle suspension, (5% w/v %; particle size 0.52 μm) were added to a 2 ml plastic tube and centrifuged at 10K rpm for 5 minutes, and the supernatant liquid was removed and discarded. 500 μl of a coating buffer was added into the particle pellet and mixed well by pipetting. The mixture was then centrifuged to remove the supernatant.

1.48 mL of G6PDH-MMA (0.638 mg/mL in coating buffer (MES 25 mM at pH5.0)) was added to the particle pellet, and the particles where re-suspended and mixed well. To coat the 0.5 μM latex particles with a mono-layer of conjugate, 34.3 μg conjugate per mg bead was used. The particle suspension and conjugate mixture was rotated end-over-end at 4° C. for 16 hours. The particle suspension was then centrifuged at 10,000 rpm for 5 minutes. The supernatant liquid was removed and filtered with a 0.2 μm filter. The conjugate residue was measured using a BCA Protein Assay Kit (Thermo Fischer) to determine the coating efficiency. The particles were washed with the coating buffer twice, and then re-suspended in coating buffer and stored at 4° C. The coated particle concentration was determined by diluting 5 μL of the above particle suspension in 995 μL water (×200 dilution) and reading at 650 nm. The $A_{650}$ was 0.348, corresponding to 1.8% of solid particles (w/v).

Example 7

Synthesis of Chemically Modified MMA-Amino-Particles

Preparation of chemically modified MMA-amino-particles is shown with the following schematic and in the following procedures. This procedure can generally be used with other arginine derivatives:

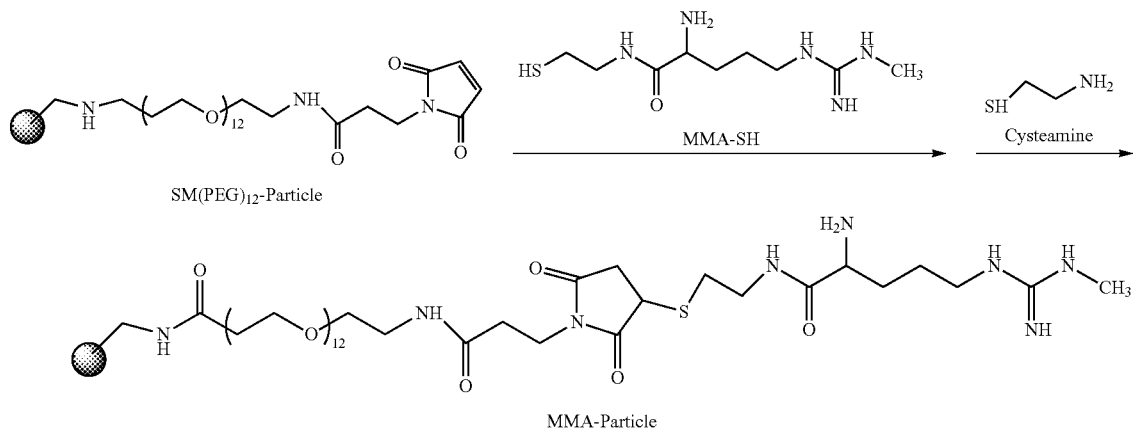

SM(PEG)12-Activation of Amino-Particles 10 ml of a suspension of amine-modified polystyrene particles (5% w/v; particle size 0.55 μm) was added into a 50 ml Falcon tube and centrifuged at 7000 rpm for 25 min, then the supernatant was discarded. The particle pellet was washed with 20 ml of phosphate buffer (50 mM at pH7.4) two times and then re-suspended into 20 ml of phosphate buffer at pH 7.4. 100 mg of the SM(PEG)12 (Thermo Fischer Pierce) was dissolved in 1 ml of DMSO to a final concentration of 100 mg/ml. In a shaker, the SM(PEG)12 solution was added to the amine particle suspension drop by drop, and then rotated end-to-end for 4 hours at 25° C. The particle mixture was washed four times by centrifugation at 7000 rpm for 20 min, resuspension in phosphate buffer (40 ml) by sonication for 1 min, and a 20 minute incubation. After the fourth wash, the particles were resuspended into 20 ml of phosphate buffer with 5 mM EDTA.

MMA-SH Conjugated to SM(PEG)12 Particles 25 mg of MMA-SH-2TFA was dissolved in 4.2 ml of 5 mM EDTA solution to prepare a 12.5 mM MMA-SH stock solution. The MMA-SH stock (12.5 mM) was diluted to 1.25 mM to prepare an intermediate MMA-SH solution, then diluted once more to 0.05 mM to prepare a MMA-SH work solution. The above SM(PEG)12-activated particle solution (10 ml) was shaken, and a corresponding volume of MMA-SH work solution (0.05 mM) was added dropwise to the particle solution. The particles were mixed well by sonication and then rotated end-over-end at 25° C. for 15 hours. Cysteamine at 5 mM was added and incubated with the particle for another 1hr. The particles were then centrifuged at 6000 rpm for 15 min and washed with 12 ml of phosphate buffer five times by sonication and resuspension. The particles were then resuspended into 10 ml of phosphate buffer. To measure the particle concentration, the suspension was diluted 200 times in deionized water and the OD was read at 650 nm.

Example 8

Preparation of Particle Spotting Diluent

For 500 ml scale, the following materials were mixed, and the final pH of the liquid was adjusted to 7.4.
50 ml 1 M Phosphate Buffer
50 grams of sucrose
20 µl TWEEN® 20 surfactant
450 ml deionized Water Example 9

Synthesis of Anti-SDMA-Antibody-HRP Conjugates

Figure 14:
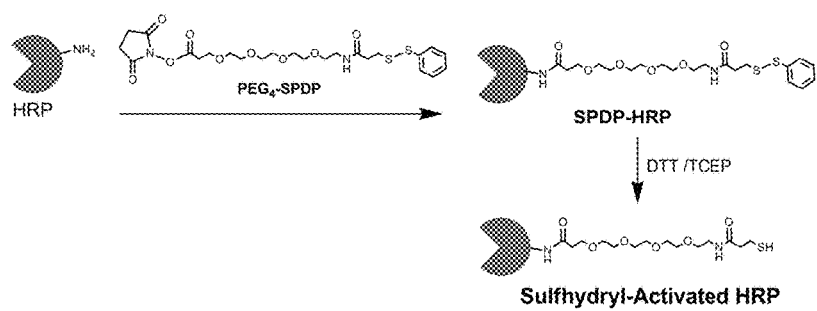
FIG. 14 shows the alternative steps for the synthesis of Anti-SDMA-Antibody-HRP Conjugates from Example 9.
Figure 14:
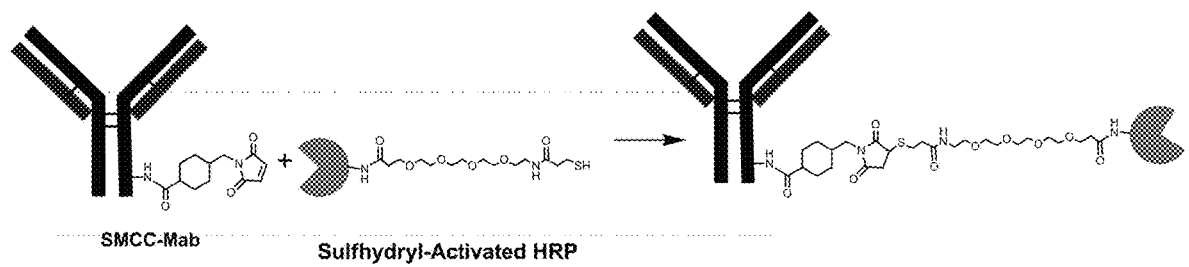

A four-step reaction scheme was used to prepare anti-SDMA antibodies and HRP conjugates via Sulfo-activation of antibodies and Traut's reagent or SPDP reagent activation of enzyme horseradish peroxidase (HRP). In step 1, maleimide was used to cap any free thiol fragments in the antibody solution to avoid crosslinking of antibodies during the SMCC activation process. In step 2, an SMCC crosslinker was reacted with the antibody to produce a maleimide-activated antibody (SMCC-Mab). In step 3, after excess non-reacted crosslinker was removed by dialysis, SMCC activated antibody was reacted with a sulfhydryl activated HRP, which was prepared either by activation of the HRP with Traut's reagent or by SPDP. The SMCC-Activated antibody reacts with HRP enzyme by sulfhydryl groups. The chemical route of synthesis of Mab-HRP is show in the following schematic (steps 3 and 4 represented by either activation of HRP with Traut's reagent or by SPDP):

Alternatively, steps 3 and 4 can be completed as shown in FIG. 14.

Procedures for steps 1-4 are shown more particularly below:

Step 1: Maleimide Capping of Impurity Free Thiols

To 4 ml of 5.6 mg/mL Anti-SDMA Mab (prepared as in U.S. Pat. No. 8,481,690) (total 22.4 mg) in PBS, 15 µl of 0.5 M maleimide in DMSO was added and then rotated end-over-end for 45 min at room temperature. The capped antibody solution was dialyzed against PBS (4 L) three times at 4° C. Antibody concentration was determined by 10-fold dilution of antibody with PBS and reading OD 280 nm ($OD_{280}$=1.37 is equal to 1 mg/ml) as 5.2 mg/ml.

Step 2: SMCC Activation of Anti-SDMA Mab

50 µl of Sulfo-SMCC (No Weight Format, equilibrated vial to room temperature before opening to avoid moisture condensation, 2 mg was added 100 µl DMSO to make 10.0 mg/ml solution) was then added into 3.3 ml of the maleimide-capped Mab in PBS at 5.2 mg/ml, which was mixed gently and rotated end-over-end (gently with low speed) at room temperature for 1 hr. The SMCC activated antibody was dialyzed against PBS (4 L) three times at 4° C. The concentration of the SMCC-activated antibody (SMCC-Ab) was determined by a 10-fold dilution of the antibody with PBS, and then reading OD at 280 nm as 4.9 mg/ml.

Step 3 (Alternative 1): Traut's Reagent Activation of HRP 40 mg of HRP was dissolved in 3 ml of PBS with 5 mM EDTA and the final concentration of HRP was 13.3 mg/ml. 0.275 ml of Traut's reagent (20 eq) in water (10 mg/ml) was added to the above HRP solution, and then rotated end-over-end for 1 hr at 25° C. The solution was then desalted by PD-10 column and washed with a PBS buffer including 5 mM EDTA. Fractions with a brown color were collected, and the OD at 405 nm was measured to determine an HRP concentration of 7.8 mg/ml Step 3 (Alternative 1): Preparation of Antibody-HRP Traut Conjugate 0.7 ml of SMCC-Mab in PBS (2.23 mg/ml) was added to an EDTA solution (0.5 M at pH8.0) to achieve a final EDTA concentration of 5 mM. 0.64 ml of Traut-HRP (12 Eq, 7.8 mg/ml), purified above, was added, and then the mixture was rotated end-over-end at 4° C. for 24 hours. Cysteine (0.5 M) was added to the mixture at a final concentration of 0.5 mM to quench the reaction, and the mixture was allowed to stand at room temperature for 2 hours. The prepared conjugate solution was then filtered by a 0.2 µm spin filter. The conjugate was stored at 4° C., and SDS-PAGE and SEC were used to characterize the conjugates present in the solution.

Step 3 (Alternative 2): SPDP Activation of HRP 250 mg of HRP was dissolved in 12.5 ml of PBS to make a 20 mg/ml solution. 100 mg of PEG4-SPDP (PEGylated, long-chain SPDP crosslinker; SPDP is succinimidyl 3-(2-pyridyldithio)propionate)(Thermo Fisher Scientific) was allowed to cool to room temperature and was then dissolved in 1 ml of DMSO to make a 100 mg/ml PEG4-SPDP solution. 0.7 ml of the SPDP solution was then added to 12.5 ml of the HRP solution and rotated end-over-end for 1hr at room temperature. The SPDP-HRP conjugate was dialyzed three times against PBS (4 L) at 4° C. A HRP concentration of 15.2 mg/ml was determined via an OD reading at 405 nm of a 20-fold dilution of the SPDP-HRP solution.

De-Capping of SPDP-HRP by TCEP Resin 6 ml of TCEP resin slurry was centrifuged (3000 rpm for 2 min) and the supernatant was discarded. The resin pellet was then washed two times with 6 ml of PBS buffer containing 5 mM EDTA. 40 µl of 0.5 M EDTA solution was then added to 4 ml of the SPDP-HRP solution (15.2 mg/ml), mixed well, and then added to the TCEP resin. This solution was then mixed well and rotated end-over-end for 2 hours at room temperature. After the resins were filtered off, the concentration of HRP was determined by a 20-fold dilution and an OD reading at 405 nm, giving a concentration of 10.5 mg/ml.

Step 4 (Alternative 2): Antibody-HRP SPDP Conjugate 2.2 ml of SMCC-mAb in PBS (4.9 mg/ml) was added to EDTA to prepare a 5 mM mixture. To this mixture, 2.2 ml of the De-capped SPDP-HRP (10.5 mg/ml, 8 Eq of HRP/Ab) was added, mixed well, and then rotated end-over-end for 15 hours at 4° C. To quench the SMCC reaction, 4.4 µl of 0.5 M Cysteine in water at 0.5 mM was added and incubated for 2 hours at 4° C. To block the free thiols, 4.4 µl of 0.5 M Cysteine in DMSO at 1 mM was added and then incubated for 1 hour at 4° C. The prepared conjugate solution was then filtered by 0.2 µm spin filter and stored at −80° C. SDS-PAGE and SEC were used to analyze the conjugate.

Example 10

Preparation of Anti-SDMA Liquid Conjugate Reagent

Anti-SDMA bulk conjugate solution was prepared in conjugate diluent as described in Example 11. Anti-SDMA antibody conjugate was pre-diluted to 50 µg/mL using the conjugate diluent. To prepare working solution, the bulk conjugate solution (50 µg/ml) was added to conjugate diluent to a final concentration of 0.3 or 0.8 µg/ml. The working solution was then mixed well by rotating the solutions at 25° C. for 30 min. The working solution was then wrapped in foil and stored at 4° C. until use.

Example 11

Preparation of Conjugate Reagent Diluent

The following materials were added to 150 mL of STA-BLZYME SELECT® stabilizer in the order listed. The mixture was then mixed by rotating at 25° C. for 2 hours, and the pH was adjusted to 7.0.
 180 mg ANS
 2.625 g salicylic acid
 17.5 g sucrose
 16.5 mg heparin
 50 mg inactive HRP
 0.5 mL blue dye The above materials were added to 250 mL of STA-BLZYME SELECT® stabilizer and gently mixed end over end for a few minutes. The diluent was filtered through 0.2 um filter and then covered with aluminum and stored at 4° C.

Example 12

Preparation of SDMA Assay Slides for CATALYST DX® Analyzer

Stored G6PDH-MMA or G6PDH-ADMA passively coated latex particles were mixed into spotting diluent (Example 8) at a final particle concentration of 0.1%. 35 µL of diluted particle solution was added onto each slide pre-assembled (see US 2014/0315216) with a Fusion 5 single layer matrix membrane (GE Healthcare Life Sciences). The slides were then dried in a drying tunnel at 49° C. and a flow rate of 745 for 30 min. The dried slides were put into a foil bag with a desiccant and the bag containing the slides was sealed and stored at 4° C.

To prepare the slide using MMA-amino-particles, the particles as described in Examples 6 and 7 were diluted into the spotting diluent at a final particle concentration of 0.1% and then spotted on the slides and dried using the above drying procedure.

Example 13

SDMA Assay on CATALYST DX® Analyzer

The Catalyst DX® assays were performed according the following general procedure and according the instruction of the manufacturer (IDEXX Laboratories, Inc.) The sample and the anti-SDMA-HRP conjugate were incubated for two minutes at room temperature. Two 11 aliquots of the mixture were applied to the CATALYST DX® solid phase prepared as described in Example 12. The solid phase was washed three times with 9 µL of wash buffer. Two 11.5 µL aliquots of TMB substrate were added. The OD of the slide was then read for two minutes at 0.5 second intervals at 645 nM.

FIG. 1 shows SDMA calibration curves using protein G6PDH-MMA passively-coated latex particles as solid phase and Anti-SDMA SPDP HRP conjugates. SDMA calibrators were prepared in un-stripped canine serum. Solid Phase: Particle concentration (0.1%); Liquid Conjugate=0.3 µg/ml.

Figure 1B:
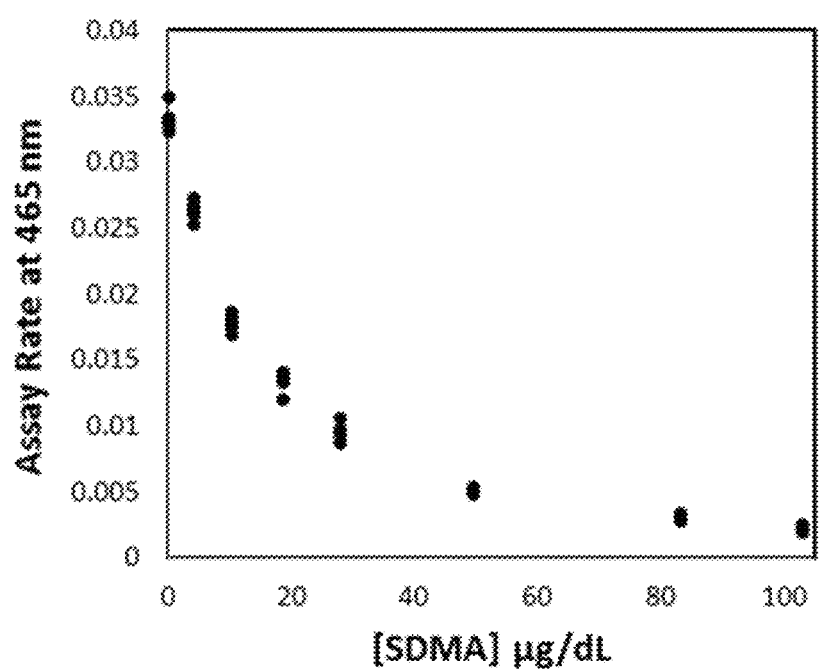

FIG. 1B shows an SDMA calibration plot using protein G6PDH-MMA passively-coated latex particles as solid phase and anti-SDMA SPDP HRP conjugate. SDMA calibrators were prepared in un-stripped canine serum. Solid Phase: Particle concentration (0.025%); Liquid Conjugate=0.027 µg/ml. Data shown represents six repetitions of the experiment.

Figure 2:
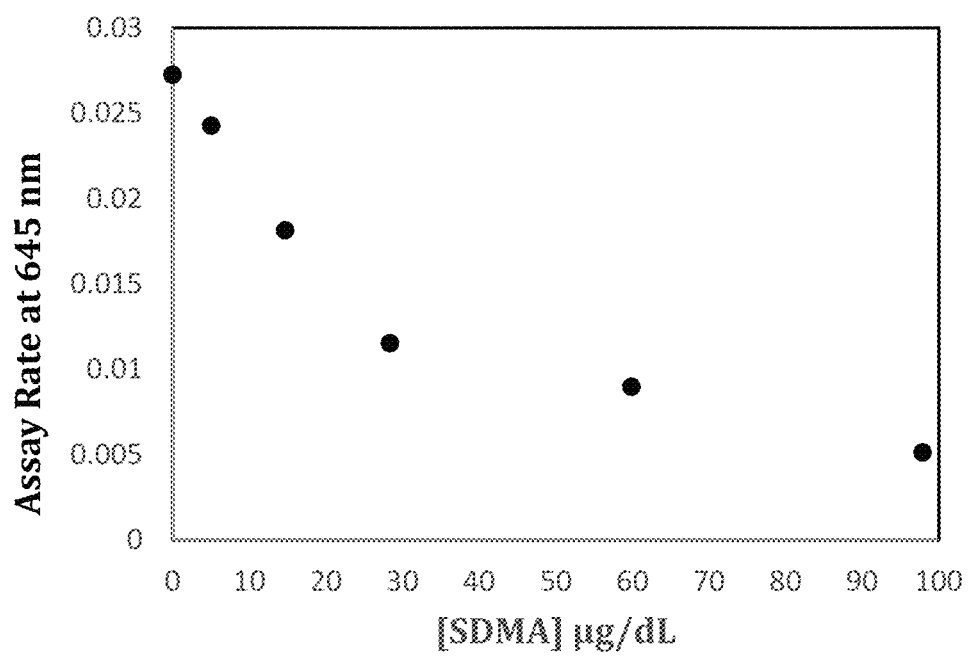
FIG. 2 shows SDMA calibration curves prepared according to methods of the disclosure using KLH-MMA coated particles as solid phase and Anti-SDMA SPDP HRP conjugate.
Figure 3:
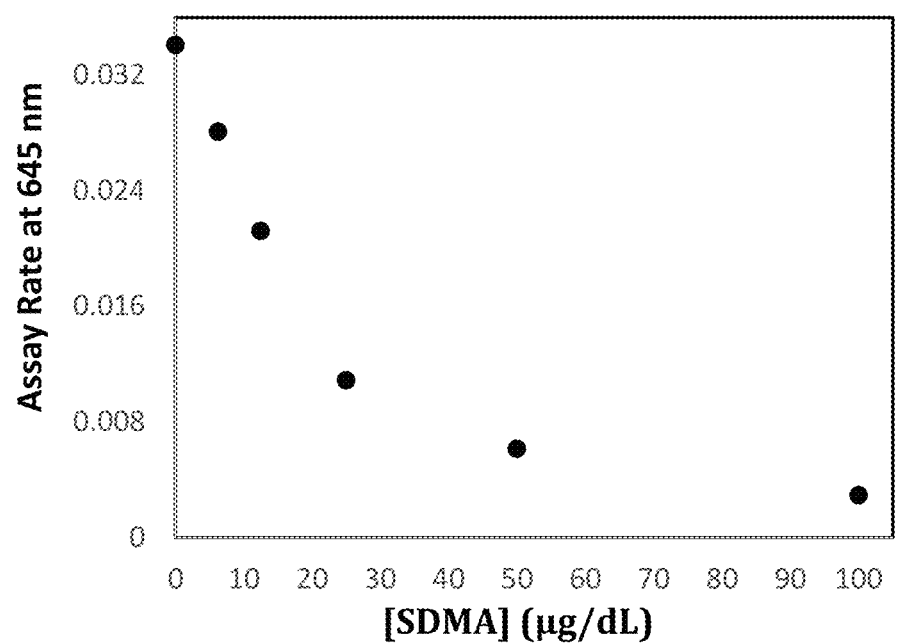
FIG. 3 shows SDMA calibration curves prepared according to methods of the disclosure using MMA chemically-modified particles as solid phase and anti-SDMA SPDP HRP conjugate.
Figure 4:
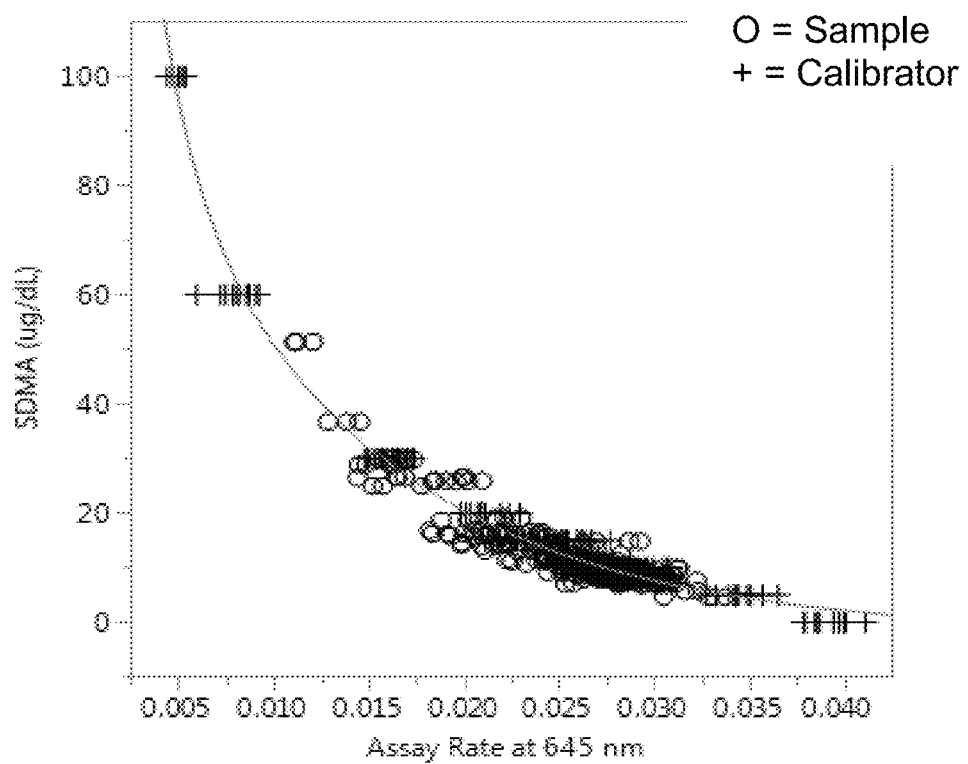
FIG. 4 shows a sample analysis prepared according to methods of the disclosure using G6PDH-MMA particle solid phase and liquid SPDP conjugate.

FIG. 2 shows SDMA calibration curves using KLH-MMA passively-coated particles as solid phase and Anti-SDMA SPDP HRP conjugates. SDMA calibrators were prepared in un-stripped canine serum. Solid Phase: Particle concentration (0.1%); Liquid Conjugate=0.8 µg/ml FIG. 3 shows SDMA calibration curves using MMA chemically-modified particles as solid phase and anti-SDMA SPDP HRP conjugates. SDMA calibrators were prepared in un-stripped canine serum. Solid Phase: Particle concentration (0.1%); Liquid Conjugate=0.8 µg/ml FIG. 4 shows CATALYST DX® SDMA sample analysis of calibrators and patient samples using G6PDH-MMA passively-coated particle solid phase and liquid SPDP conjugates.

Example 14

Comparison of Solid Phase Properties of SDMA, ADMA and MMA Coated Particles

To develop a Catalyst Analyzer-based SDMA assay, different versions of solid phases were developed, including solid phases having immobilized particles passively coated with protein-based MMA, ADMA and SDMA conjugates as described in Example 1 and 12. Immobilized particles chemically-modified with MMA and SDMA as described in Example 7 were also investigated.

One finding is that the assay performance is improved with MMA immobilized and used on the solid phase. Use of SDMA immobilized on the solid phase, either by protein-based passively coated latex particles or chemically-modified particles, resulted in only limited separation between the SDMA calibrator panels. MMA chemically-modified latex particles gave a calibration curve with improved assay performance, including assay precision and accuracy, but suffered large bias between the two sample types, serum and plasma. The best Catalyst SDMA assay performance was provided by G6PDH-MMA conjugates passively coated on particles that were immobilized on the solid phase. The particles resulted in an assay with excellent precision, accuracy, and stability.

The Anti-SDMA-enzyme conjugates were also investigated using Traut's Reagent or SPDP as described in Example 9. The formed conjugates were shown to provide a broad dynamic range in the SDMA assay and improved assay performance.

As shown in Table 1, the coating efficiency of BSA-MMA/BSA-SDMA on latex particles (~25%) was much lower than the coating efficiency for KLH-MMA/KLH-SDMA and G6PDH-MMA/G6PDH-SDMA (~95%). The KLH-MMA and KLH-SDMA coated latex particles aggregated under storage conditions before they were spotted on the slides, resulting in a large variation of the assay unless the particles were well-sonicated before spotting. KLH-MMA was stable if directly spotted on the Fusion 5 slides when the slides were incubated under 37° C. for one week, but were not stable when incubated for two weeks. G6PDH-MMA had high coating efficiency on latex particles, and was very robust on dried slides, even when incubated under 37 C for two weeks, thus providing the best solid phase for SDMA Catalyst assay.

TABLE 1

| Solid Phase | Coating Efficiency on latex particle (%) | Particle Aggregation | Slide Stability Under 37° C. |
|---|---|---|---|
| G6PDH-MMA | 95 | No | Stable over 14 Days |
| G6PDH-SDMA | 98 | No | Not determined |
| KLH-MMA | 95 | Yes | Stable for 7 days |
| KLH-SDMA | 96 | Yes | Not determined |
| BSA-MMA | 30 | No | Not determined |
| BSA-SDMA | 22 | No | Not determined |

Table 2 shows a comparison of assay performance using solid phase with passively-coated KLH-MMA and KLH-SDMA particles.

TABLE 2

| Solid Phase | Particles on Slide (%) | Liquid Reagent [Conjugate] µg/ml | Assay Rate for Cal0 [SDMA] = 0 µg/dL | Assay Rate for Cal4 [SDMA] = 59.9 µg/dL | Assay Rate Change (%) |
|---|---|---|---|---|---|
| KLH-MMA | 0.05 | 0.2 | 0.027755 | 0.006454 | 77 |
| KLH-MMA | 0.1 | 0.2 | 0.039346 | 0.023397 | 41 |
| KLH-SDMA | 0.05 | 0.2 | 0.021413 | 0.009627 | 55 |
| KLH-SDMA | 0.1 | 0.2 | 0.036312 | 0.02749 | 24 |

Table 3 shows a comparison of assay performance using solid phase with immobilized particles having passively-coated G6PDH-MMA, G6PDH-ADMA and G6PDH-SDMA.

TABLE 3

| Solid Phase | Particles on Slide % | Liquid Reagent [Conjugate] µg/ml | Assay Rate for Cal0 [SDMA] = 0 µg/dL | Assay Rate for Cal4 [SDMA] = 0 µg/dL | Assay Rate Change (%) |
|---|---|---|---|---|---|
| G6PDH-MMA | 0.03 | 0.6 | 0.021232 | 0.004854 | 77 |
| G6PDH-SDMA | 0.03 | 0.25 | 0.034884 | 0.027355 | 22 |
| G6PDH-MMA | 0.03 | 0.3 | 0.027160 | — | — |
| G6PDH-ADMA | 0.03 | 0.3 | 0.001056 | — | — |
| G6PDH-ADMA | 0.03 | 5.0 | 0.014504 | — | — |

As shown in Table 3, immobilized particles having passively-coated G6PDH-MMA, G6PDH-ADMA or G6PDH-SDMA can each be used in a Catalyst SDMA assay.

Table 4 shows a comparison of assay performance using solid phase with immobilized particles having passively-coated BSA-MMA and BSA-SDMA.

TABLE 4

| Solid Phase | Particles on Slide % | Liquid Reagent [Conjugate] µg/ml | Assay Rate for Cal0 [SDMA] = 0 µg/dL | Assay Rate for Cal4 [SDMA] = 59.9 µg/dL | Assay Rate Change (%) |
|---|---|---|---|---|---|
| BSA-MMA | 0.1 | 0.8 | 0.021580 | 0.007530 | 65 |
| BSA-SDMA | 0.1 | 0.8 | 0.015287 | 0.012183 | 20 |

Example 15

Analysis of Assay Performance

The CATALYST DX® SDMA test performance was compared to LC-MS and EMIT® assays (see US Patent Publication No. 2016/245801) for both canine samples and feline samples.

Figure 5A:
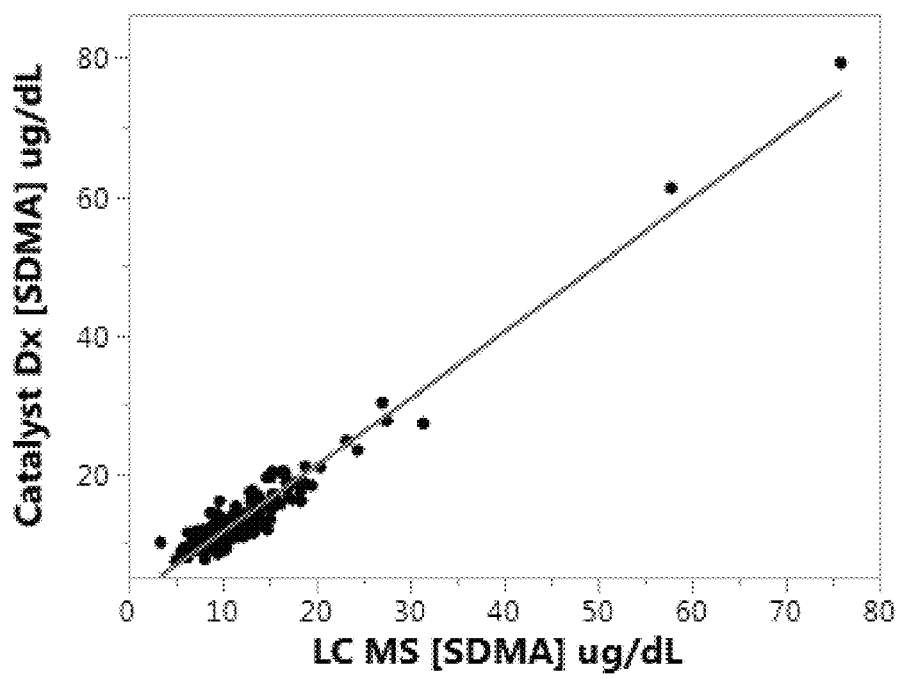
FIG. 5A shows the correlation of Catalyst DX® SDMA assays according to methods of the disclosure with LC-MS assays for 207 canine serum samples.

FIG. 5A shows the correlation of the CATALYST DX® SDMA test with LC-MS Assays for canine serum samples (207 samples). Catalyst [SDMA] (μg/dL)=1.22065+0.93353 LC-MS [SDMA] (μg/dL) with $R^2$=0.945. The R-squared value indicates that the test results were strongly correlated.

Figure 5B:
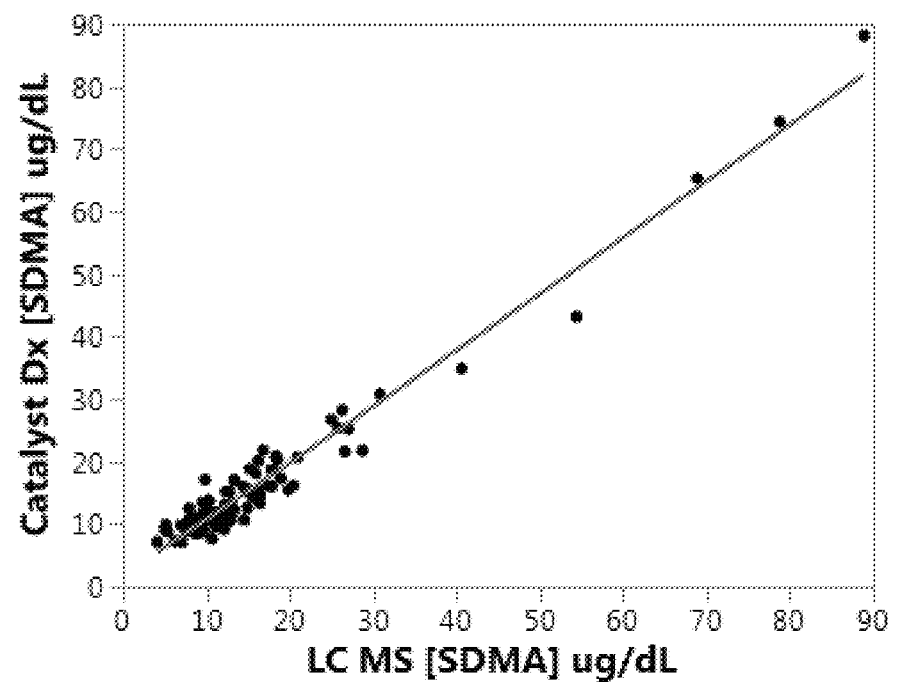
FIG. 5B shows the correlation of Catalyst DX® SDMA assays according to methods of the disclosure with LC-MS assays for 86 feline serum samples).

FIG. 5B shows the correlation of the CATALYST DX® SDMA Test with LC-MS Assays for feline serum samples (86 samples). Catalyst [SDMA] (μg/dL)=1.22065+0.93353 LC-MS[ SDMA] (μg/dL) with $R^2$=0.945. The R-squared value indicates that the test results were strongly correlated.

Figure 6A:
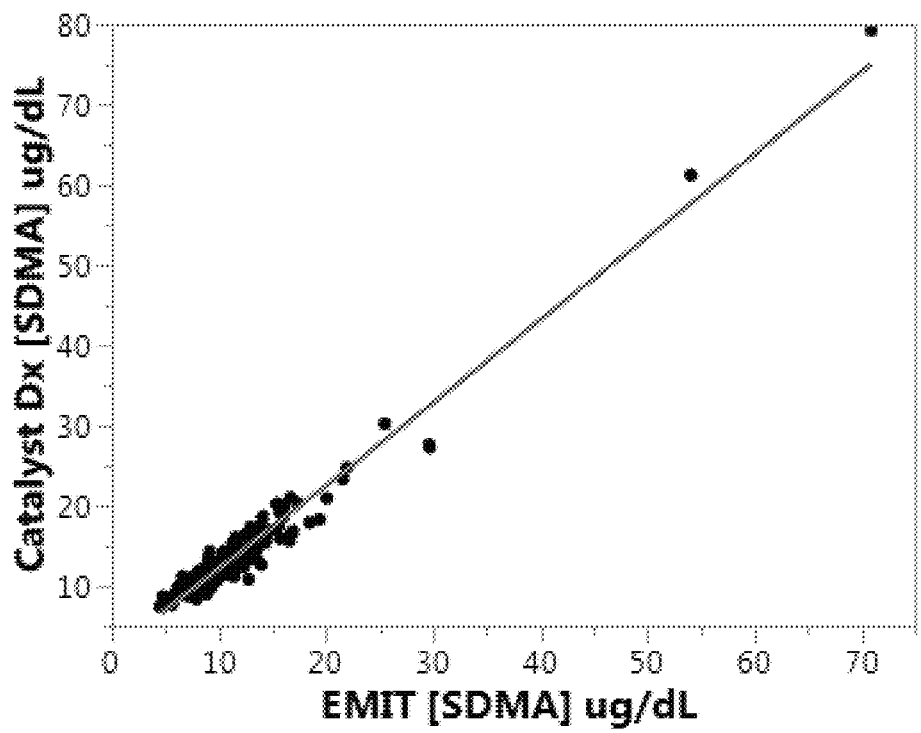
FIG. 6A shows the correlation of Catalyst DX® SDMA assays according to methods of the disclosure with EMIT® assays for 207 canine serum samples.

FIG. 6A shows the correlation of CATALYST DX® SDMA Test with EMIT Assays for canine serum samples (207 samples). Catalyst [SDMA] (μg/dL)=0.56438+0.93980 EMIT [SDMA] (μg/dL) with $R^2$=0.939. The R-squared value indicates that the test results were strongly correlated.

Figure 6B:
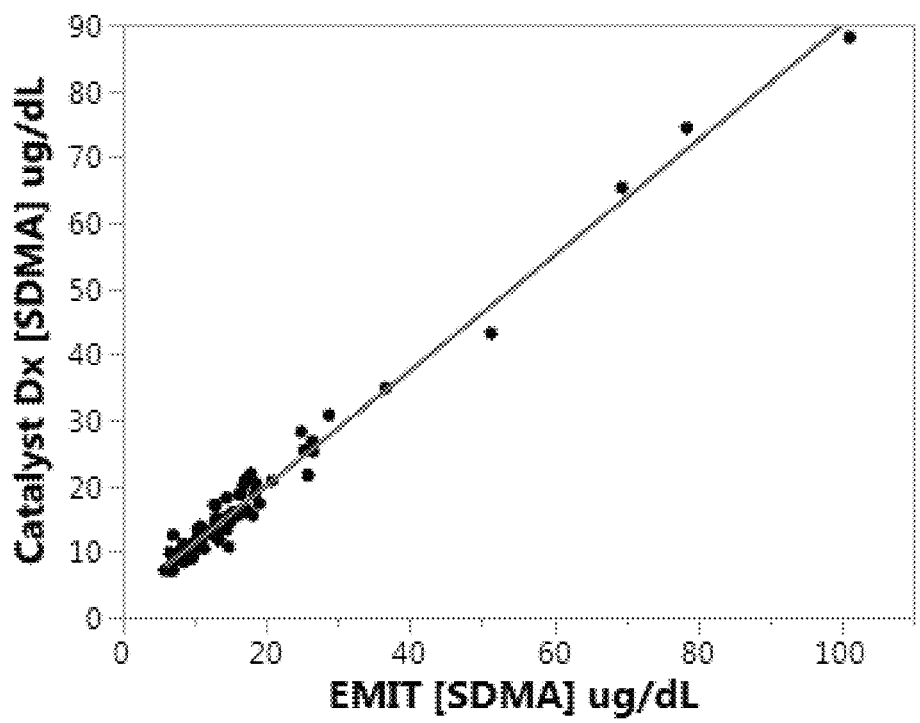
FIG. 6B shows the correlation of Catalyst DX® SDMA assays according to methods of the disclosure with EMIT assays for 86 feline serum samples.

FIG. 6B shows the correlation of CATALYST DX® SDMA Test with EMIT Assays for feline serum samples (86 samples). Catalyst [SDMA] (μg/dL)=0.56438+0.93980 EMIT [SDMA] (μg/dL) with $R^2$=0.939. The R-squared value indicates that the test results were strongly correlated.

Example 16

Comparison of Serum/Plasma Bias in Covalently Linked Amine-MMA Particles and Passively Coated G6PDH-MMA Particles The Catalyst DX® SDMA assay was carried out on matched serum and plasma samples, with either covalently linked amine-MMA particles or passively coated G6PDH-MMA particles. The experiments were performed in duplicate. Sample bias was calculated as follows: (serum SDMA (μg/dL)−plasma SDMA (μg/dL)/((serum SDMA (μg/dL)+ plasma SDMA (μg/dL))/2), which reflects the difference between the serum and plasma values) divided by the mean of the serum and plasma values.

Figure 7A:
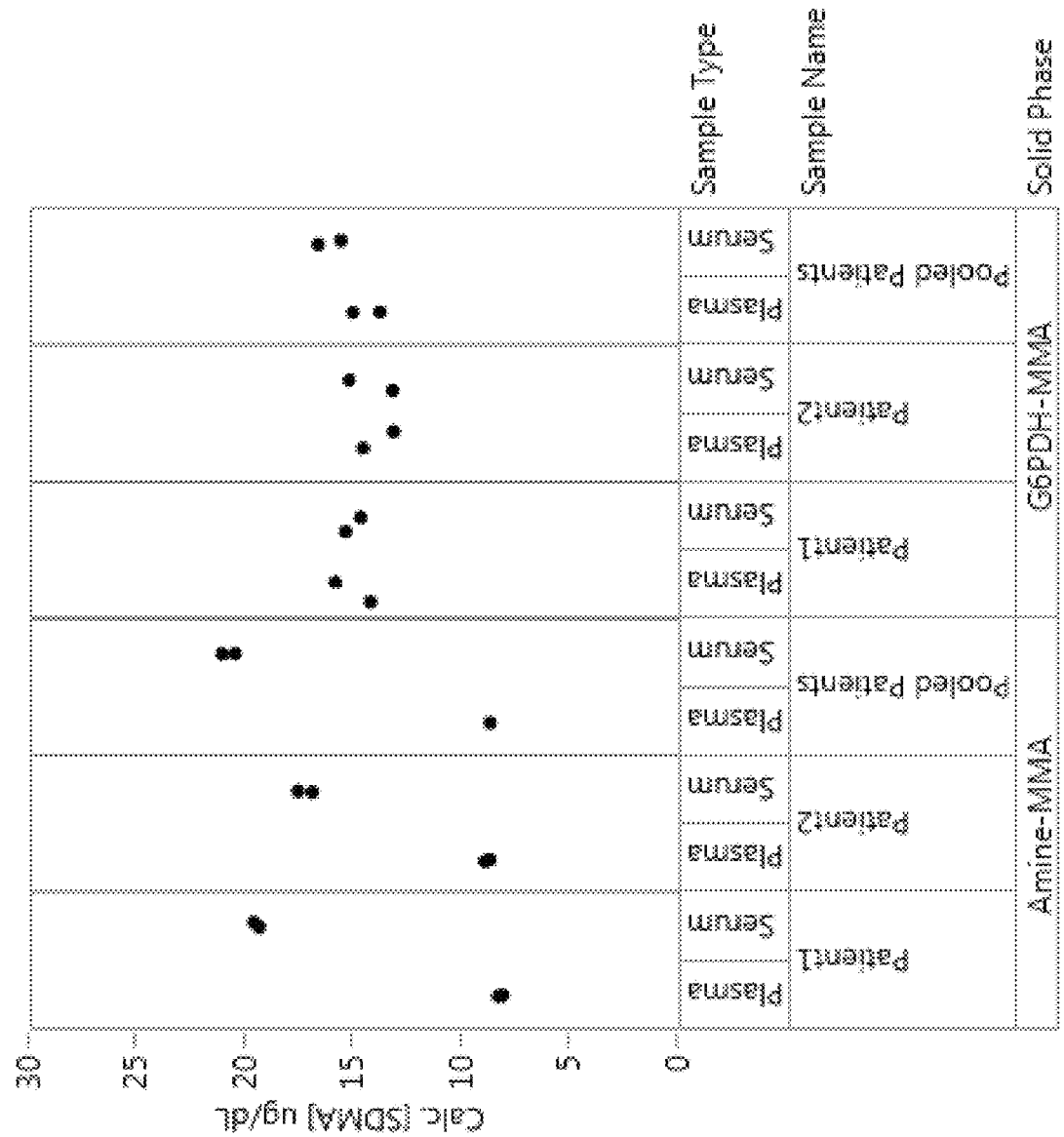
FIG. 7A shows the results of Catalyst DX® SDMA assays according to methods of the disclosure for matched canine serum and plasma samples, with either covalently linked amine-MMA particles or passively coated G6PDH-MMA particles.

As shown in Table 5 and FIG. 7A, in canine samples a serum/plasma bias of 64-82% was observed with the amine-MMA covalently linked particles. In contrast, a serum/plasma bias of 0% to 11% was observed with passively coated G6PDH-MMA particles. Therefore, the passively coated G6DPH-MMA particles greatly reduced the plasma/serum bias observed in canine samples with covalently linked amine-MMA particles.

Figure 7B:
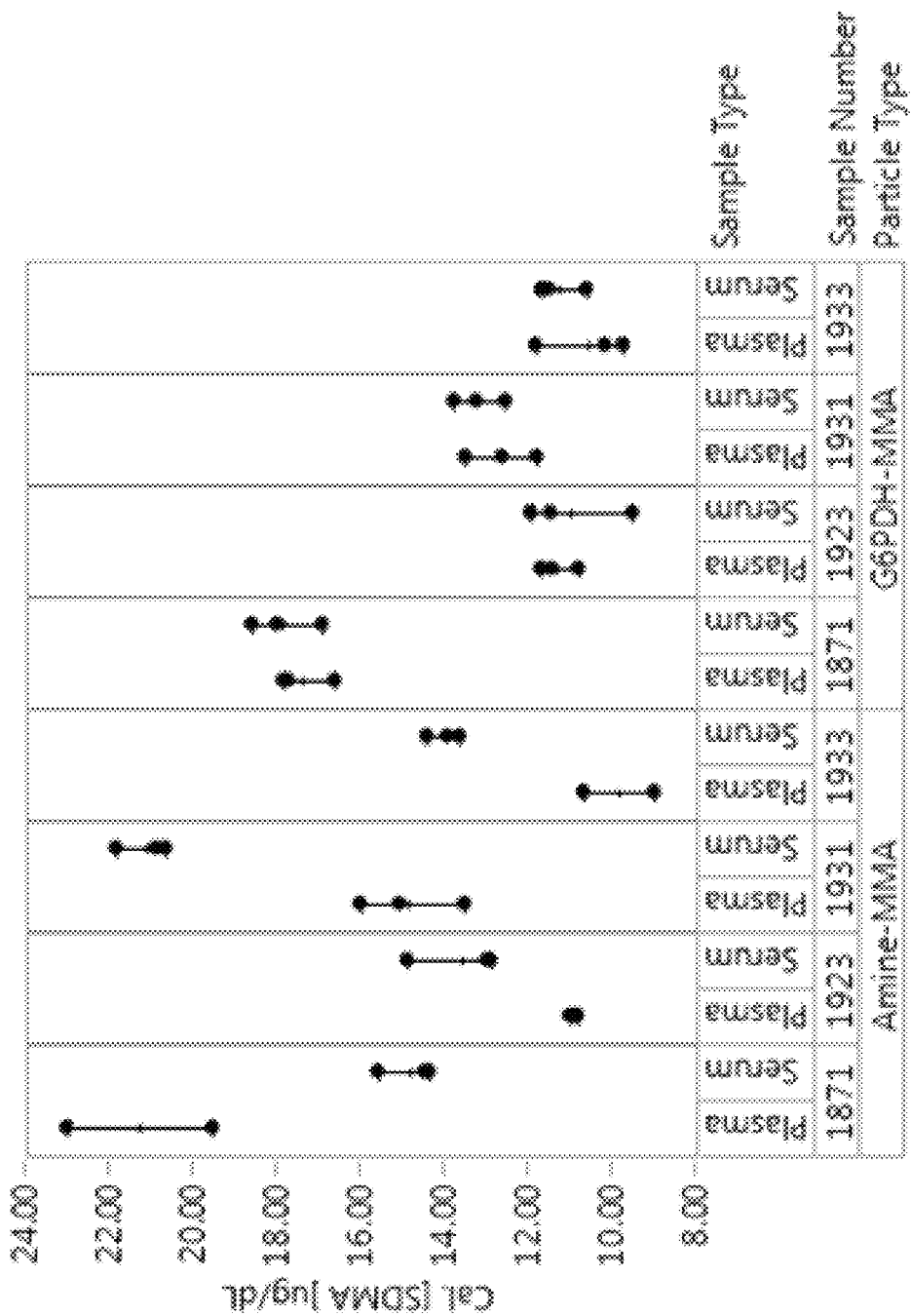
FIG. 7B shows the results of Catalyst DX® SDMA assays according to methods of the disclosure for matched feline serum and plasma samples, with either covalently linked amine-MMA particles or passively coated G6PDH-MMA particles.

As shown in Table 6 and FIG. 7B, in feline samples a serum/plasma bias of −36% to 35% was observed with the amine-MMA covalently linked particles. In contrast, a serum/plasma bias of −3% to 6% was observed with passively coated G6PDH-MMA particles. Therefore, the passively coated G6DPH-MMA particles greatly reduced the plasma/serum bias observed in feline samples with covalently linked amine-MMA particles.

TABLE 5

| Particles | Sample Name | Sample Type | Calc. [SDMA] μg/dL | Bias |
|---|---|---|---|---|
| Amine-MMA | Patient1 | Plasma | 8.2 | 81% |
| | | Serum | 19.5 | |
| | Patient2 | Plasma | 8.9 | 64% |
| | | Serum | 17.3 | |

TABLE 5-continued

| Particles | Sample Name | Sample Type | Calc. [SDMA] μg/dL | Bias |
|---|---|---|---|---|
| | Pooled Patients | Plasma | 8.7 | 82% |
| | | Serum | 20.8 | |
| G6PDH-MMA | Patient1 | Plasma | 15.1 | 0% |
| | | Serum | 15.0 | |
| | Patient2 | Plasma | 13.9 | 3% |
| | | Serum | 14.2 | |
| | Pooled Patients | Plasma | 14.4 | 11% |
| | | Serum | 16.2 | |

TABLE 6

| Particles | Sample Name | Sample Type | Calc. [SDMA] μg/dL | Bias |
|---|---|---|---|---|
| Amine-MMA | 1871 | Plasma | 21.31 | −36% |
| | | Serum | 14.83 | |
| | 1923 | Plasma | 10.93 | 22% |
| | | Serum | 13.61 | |
| | 1931 | Plasma | 14.90 | 35% |
| | | Serum | 21.16 | |
| | 1933 | Plasma | 9.86 | 35% |
| | | Serum | 14.02 | |
| G6PDH-MMA | 1871 | Plasma | 17.42 | 2% |
| | | Serum | 17.86 | |
| | 1923 | Plasma | 11.34 | −3% |
| | | Serum | 11.00 | |
| | 1931 | Plasma | 12.67 | 4% |
| | | Serum | 13.21 | |
| | 1933 | Plasma | 10.60 | 6% |
| | | Serum | 11.29 | |

Example 17

Figure 8:
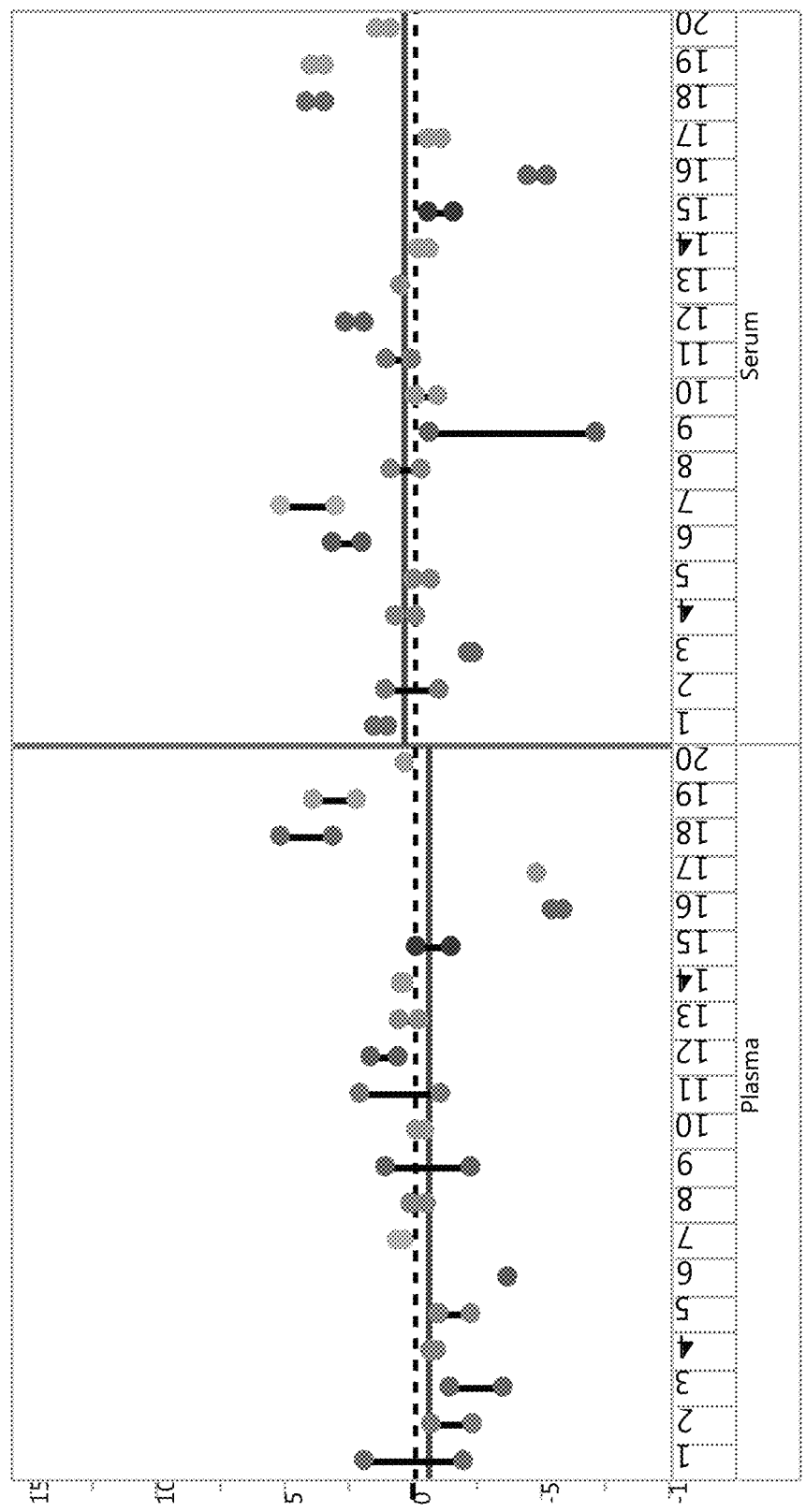
FIG. 8 shows the results of Catalyst DX® SDMA assays according to methods of the disclosure performed on 20 paired serum and plasma samples with G6PDH-MMA particles or Ovalbumin-MMA particles.
Figure 9:
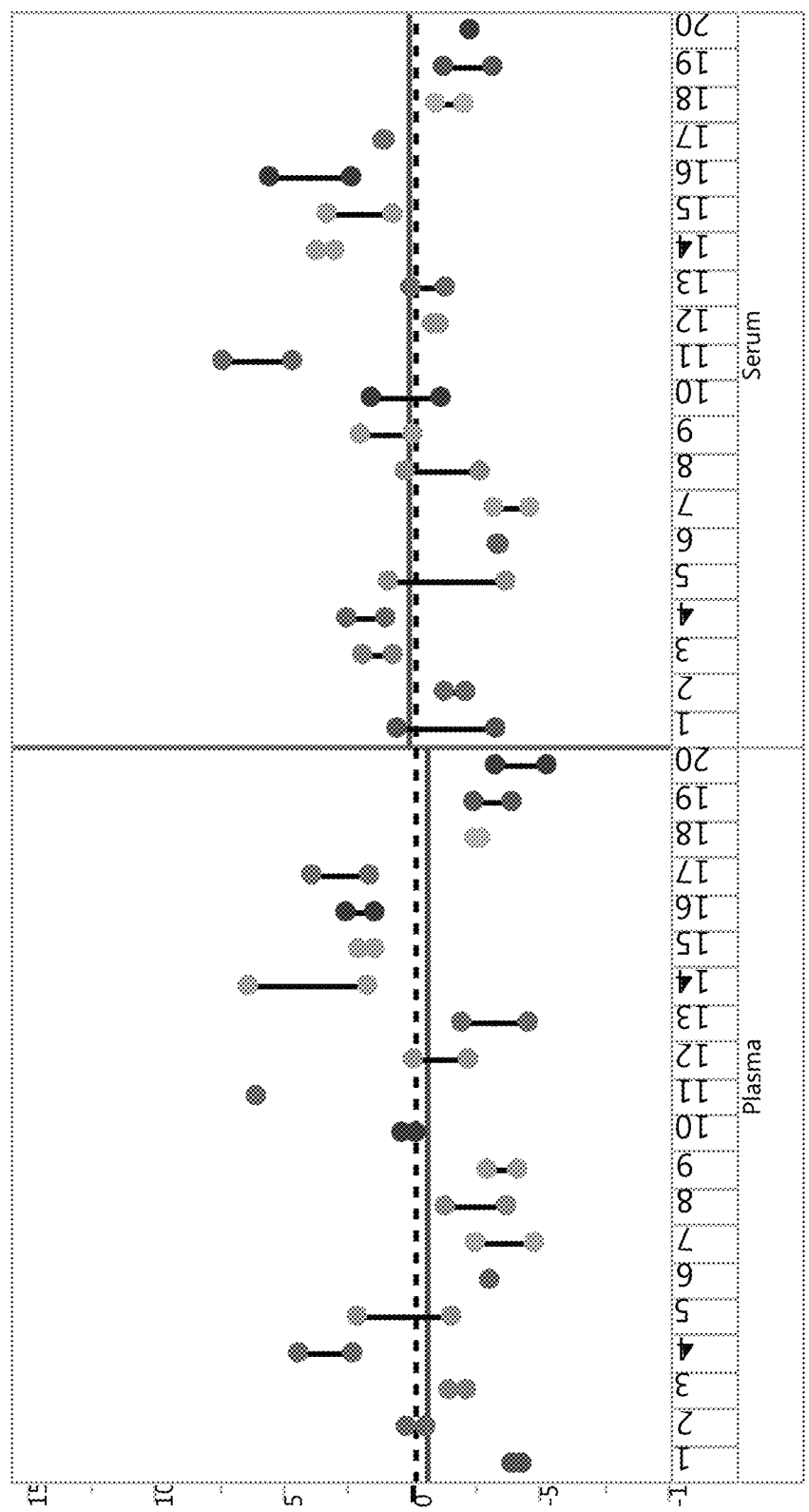
FIG. 9 shows the results of Catalyst DX® SDMA assays according to methods of the disclosure performed on 20 paired serum and plasma samples with Ovalbumin-MMA particles.

Serum/Plasma Bias in Passively Coated G6PDH-MMA Particles and Passively Coated Ovalbumin-MMA Particles The Catalyst DX® SDMA assay was performed on 20 paired canine serum and plasma samples with either G6PDH-MMA particles (FIG. 8) or Ovalbumin-MMA particles (FIG. 9). The Y-axes of the graphs in FIGS. 8 and 9 depict the difference between actual and measured SDMA concentrations in μg/dL. This difference is referred to as the "bias". The experiments were performed in duplicate. Both G6PDH and Ovalbumin coating resulted in minimal bias between SDMA values measured in serum or plasma. In addition, there was minimal bias between actual and measured SDMA values in serum samples, and a minimal bias between actual and measured SDMA values in plasma samples.

Example 18

Stability of Passively Coated Protein-MMA Particles

The stability of the protein-MMA passive coating on particles was evaluated.

Stability in Aqueous Solution

Figure 10:
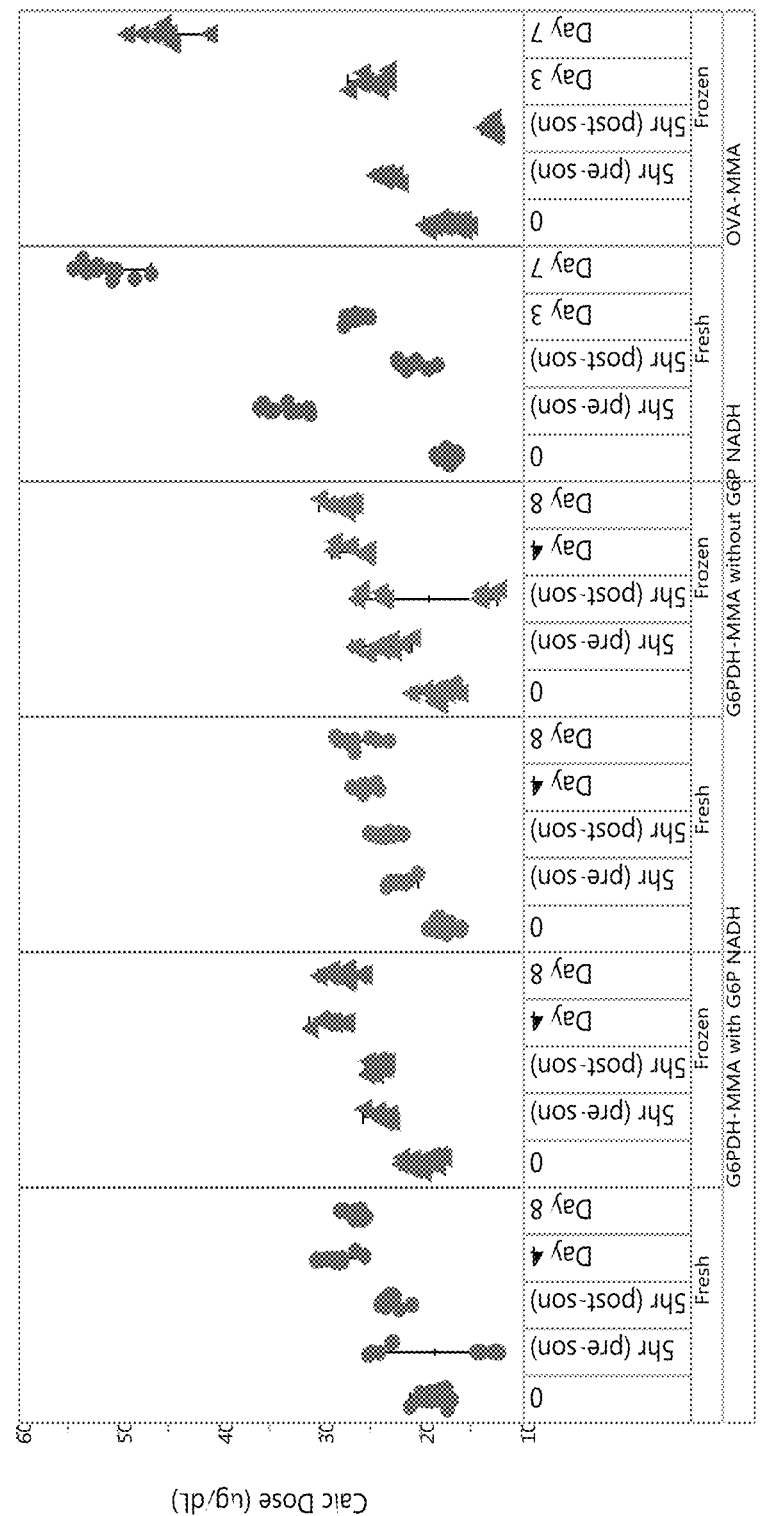
FIG. 10 shows the results of assays according the disclosure to assess stability of passively coated particles (coated with G6PDH-MMA, G6PDH-MMA or ovalbumin-MMA)

Passively coated particles (coated with G6PDH-MMA; G6PDH-MMA with its substrates G6P and NAD; or ovalbumin-MMA) were incubated at 4° C. in 50 mM sodium phosphates and 2.5% sucrose, pH6.4 for various time periods ranging from 5 hours to 8 days. An aliquot of the particles that were incubated for 5 hours were sonicated. In addition, freshly coated particles were compared to coated particles that had undergone a single freeze-thaw cycle at −20° C. Following the incubations, the particles were used in the SDMA assay, and the results are shown in FIG. 10. These preincubations had a greater effect on SDMA values when ovalbumin-MMA coated particles were used, as compared to G6PDH-MMA coated particles. These results indicate that G6PDH-MMA coated particles were more stable when incubated in an aqueous solution than the ovalbumin-MMA coated particles.

Stability in Aqueous Solution Containing High Salt Concentrations

In order to assess the tolerance of the passive coating against high salt concentrations, the SDMA assay was carried out with G6PDH-MMA passively coated particles with and without pre-treatment with 1 M NaCl overnight at 4° C. The assay was carried out with SDMA standards at 0, 6.25, 12.5, 25, 50 and 100 µg/dL SDMA.

Figure 11:
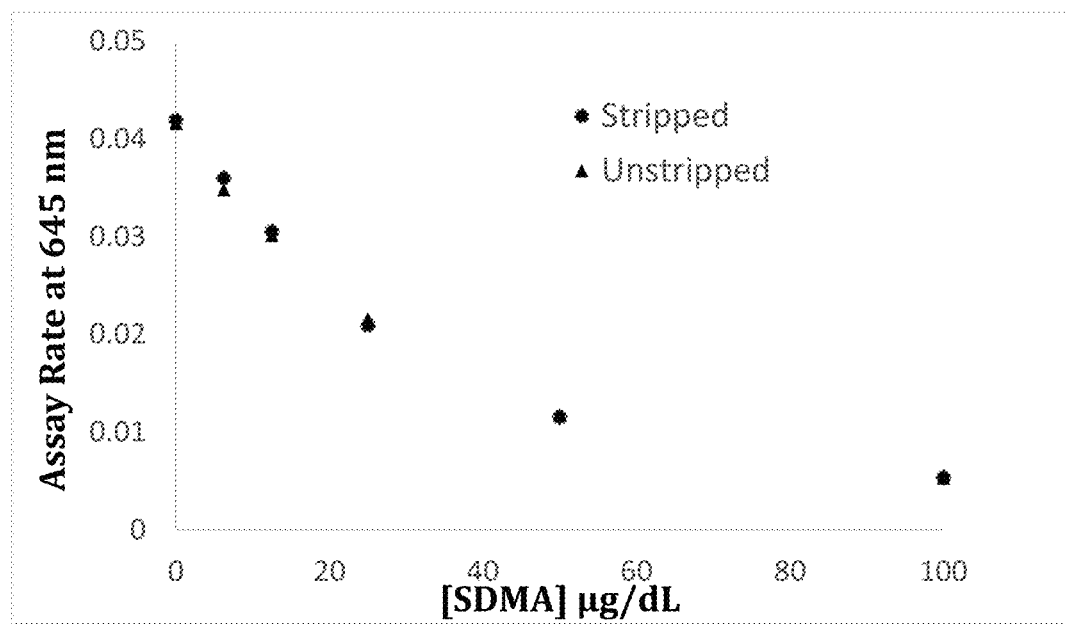
FIG. 11 shows a CATALYST DX® SDMA calibration curves using G6PDH-MMA passively coated particles with and without prior incubation with 1 M NaCl.

FIG. 11 shows a CATALYST DX® SDMA calibration curves using G6PDH-MMA passively coated particles with and without prior incubation with 1 M NaCl. The experiments were performed in triplicate. The SDMA calibration curve was indistinguishable between the particles that were exposed in 1 M sodium chloride (labeled "stripped") or the control particles (labeled "unstripped"). This indicates that the G6PDH-MMA passively coated particles are stable in 1 M sodium chloride overnight at 4° C.

Stability in Surfactant

Figure 12:
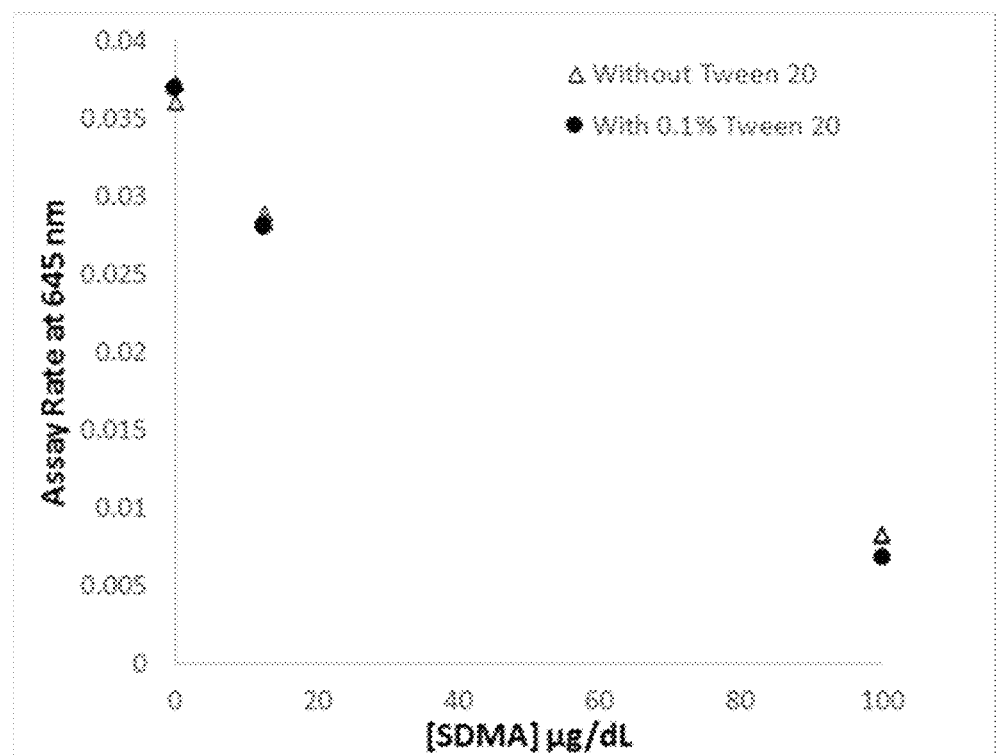
FIG. 12 shows SDMA calibration curves using G6PDH-MMA passively coated particles after pre-incubation with or without TWEEN® 20 surfactant.

G6PDH-MMA passively coated particles were incubated overnight (>12 hours) at 4° C. in buffer with or without 0.1% of the surfactant TWEEN® 20 (polyethylene glycol sorbitan monolaurate). After the overnight incubation, the particles were used in the Catalyst DX® SDMA assay. SDMA calibrators were prepared in canine serum spiked with SDMA to a final concentration of 0, 20, 40, 60, 80 or 100 µg/dL. The resulting calibration curves are shown in FIG. 12. The data indicates that the pre-incubation with the surfactant had no effect on the performance of the G6PDH-MMA passively coated particles in the assay.

Another experiment was performed to compare the surfactant tolerance of G6PDH-MMA, BSA-MMA and KLH-MMA passively coated latex particles. Each type of conjugate coated latex particle was treated with 0.1% or 1% Tween 20 in storage buffer at 4° C. overnight. The protein released into the storage buffer was measured by Micro BCA kit to determine the percentage of conjugate remaining on the particles. As shown in Table 7, among the three types of conjugate, the BSA-MMA coated latex particles were the least stable in the presence of Tween 20. In contrast, the G6PDH-MMA coated latex particles displayed the highest tolerance even when incubated with 1% Tween 20. KLH-MMA coated particles were relatively tolerant to the surfactant treatment, but the particles easily aggregated during the storage, resulting in poor assay precision.

TABLE 7

| Solid Phase | Conjugate remaining on particles with 0.1% Tween 20 | Conjugate remaining on particles with 1.0% Tween 20 |
| --- | --- | --- |
| BSA-MMA | 63% | 60% |
| KLH-MMA | 89% | 87% |
| G6PDH-MMA | 99% | 99% |

In summary, the various experiments detailed indicate that G6PDH-MMA coated latex particles showed the highest coating efficiency and stability. The G6PDH-MMA particles also remained monodispersed in storage and spotting buffers and gave the best assay performance in comparison with particles coated with other conjugates such as BSA-MMA and KLH-MMA.

Example 19

Direct Coating of KLH-MMA Onto Assay Slides

Figure 13:
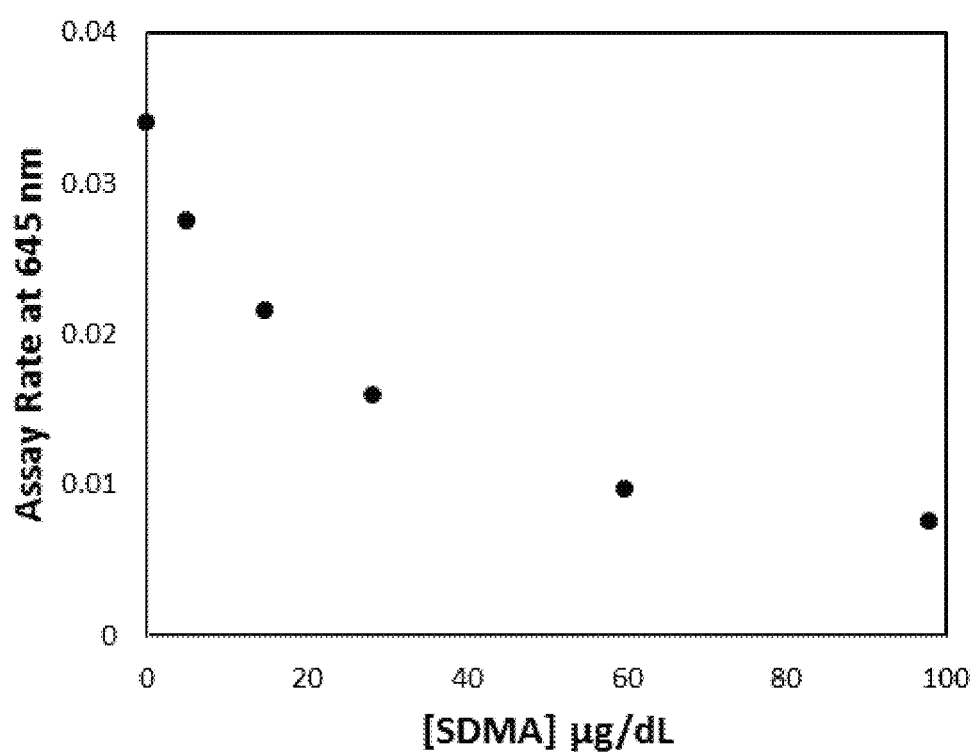
FIG. 13 shows a SDMA calibration plot using protein KLH-MMA conjugate (Example 2) coated directly onto the slide membrane.

FIG. 13 shows a SDMA calibration plot using protein KLH-MMA conjugate (Example 2) coated directly onto the slide membrane. A 35 µl aliquot of KLH-MMA conjugate (14.3 µg/ml in phosphate buffer with 2% sucrose and 0.05% Tween 20) was placed onto slides pre-assembled (see US 2014/0315216) with a Fusion 5 single layer matrix membrane (GE Healthcare Life Sciences). The slides were then dried in a drying tunnel at 49° C. and a flow rate of 745 for 30 min. SDMA calibrators were prepared in un-stripped canine serum. The calibrators were incubated with anti-SDMA-HRP Conjugate at 0.6 µg/ml for two minutes at room temperature. Two 11 µL aliquots of the mixture were applied to the slide. The solid phase was washed three times with 9 µL of wash buffer. Two 11.5 µL aliquots of TMB substrate were added. The OD of the slide was then read for two minutes at 0.5 second intervals at 645 nM. Each point on the plot represents the average results of triplicate experiments.

The examples given above are merely illustrative and are not meant to be an exhaustive list of all possible embodiments, applications or modifications of the disclosure. Thus, various modifications and variations of the described methods and systems of the disclosure will be apparent to those skilled in the art without departing from the scope and spirit of the disclosure. Although the disclosure has been described in connection with specific embodiments, it should be understood that the disclosure as claimed should not be unduly limited to such specific embodiments. Indeed, various modifications of the described modes for carrying out the disclosure which are obvious to those skilled in molecular biology, immunology, chemistry, biochemistry or in the relevant fields are intended to be within the scope of the appended claims.

It is understood that the disclosure is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the disclosure. It also is to be noted that, as used herein and in the appended claims, the singular forms "a," "an," and "the" include the plural reference unless the context clearly dictates otherwise. Thus, for example, a reference to "a linker" is a reference to one or more linkers and equivalents thereof known to those skilled in the art.

Unless defined otherwise, all technical and scientific terms used herein have the same meanings as commonly understood by one of ordinary skill in the art to which the disclosure pertains. The embodiments of the disclosure and the various features and advantageous details thereof are explained more fully with reference to the non-limiting embodiments and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein.

Any numerical values recited herein include all values from the lower value to the upper value in increments of one unit provided that there is a separation of at least two units between any lower value and any higher value. As an example, if it is stated that the concentration of a component or value of a process variable such as, for example, size, angle size, pressure, time and the like, is, for example, from 1 to 90, specifically from 20 to 80, more specifically from 30 to 70, it is intended that values such as 15 to 85, 22 to 68, 43 to 51, 30 to 32, etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Particular methods, devices, and materials are described, although any methods and materials similar or equivalent to those described herein can be used in the practice or testing of the disclosure. The disclosures of all references and publications cited above are expressly incorporated by reference in their entireties to the same extent as if each were incorporated by reference individually.

The invention claimed is:

1. A device for determining symmetrical dimethyl arginine (SDMA) in a sample, comprising a solid matrix comprising a particle non-diffusively bound thereto, wherein the particle comprises a capture reagent comprising (a) N-methylarginine (MMA) covalently attached to a protein that is attached to the particle or (b) N-methylarginine (MMA) covalently attached to the particle.

2. The device of claim 1, wherein the protein is covalently attached to the particle.

3. The device of claim 1, wherein the protein is non-covalently attached to the particle.

4. The device of claim 1, wherein the protein is at least one protein selected from the group consisting of Bovine Serum Albumin (BSA), ovalbumin, Keyhole Limpet Hemocyanin (KLH), and Glucose-6-Phosphate Dehydrogenase (G6PDH).

5. The device of claim 4, wherein the protein is G6PDH.

6. The device of claim 5, wherein the G6PDH is derived from a eukaryote, a prokaryote, a yeast or recombinant expression.

7. The device of claim 1, wherein the solid matrix is a porous matrix.

8. The device of claim 7, wherein the solid matrix is arranged in a cartridge or housing.

9. A method of determining symmetrical dimethyl arginine (SDMA) in a sample, comprising
(a) forming a mixture comprising the sample and a labeled conjugate comprising an anti-SDMA antibody conjugated to a label;
(b) contacting the mixture with the device of claim 1;
(c) washing the solid matrix to remove conjugate that is not bound to the solid matrix; and
(d) measuring the amount of the label associated with the solid matrix to determine the presence or amount of SDMA in the sample.

10. A capture reagent comprising N-methylarginine (MMA) attached to a particle.

11. The capture reagent of claim 10, wherein the MMA is bound to the particle through a linker.

12. The capture reagent of claim 11, wherein the linker comprises the following structure:

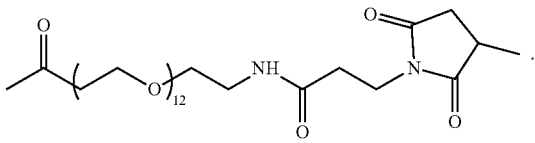

13. The capture reagent of claim 12, comprising:

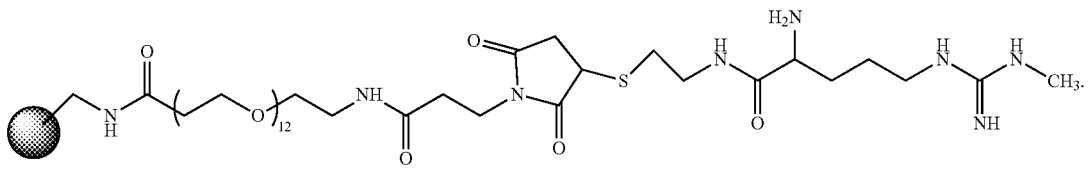

14. The capture reagent of claim 10, wherein the MMA is covalently attached to a protein that is attached to a particle.

15. The capture reagent of claim 14, wherein the protein is covalently attached to the particle.

16. The capture reagent of claim 14, wherein the protein is non-covalently attached to the particle.

17. The capture reagent of claim 14, wherein the protein is at least one protein selected from the group consisting of Bovine Serum Albumin (BSA), ovalbumin, Keyhole Limpet Hemocyanin (KLH), and Glucose-6-Phosphate Dehydrogenase (G6PDH).

18. A method of determining symmetrical dimethyl arginine (SDMA) in a sample, comprising
(a) forming a mixture comprising the sample and an anti-SDMA antibody;
b) contacting the mixture with a solid matrix comprising the capture reagent of claim 10;
(c) washing the solid matrix to remove the anti-SDMA antibody that is not bound to the solid matrix; and
(d) measuring the amount of the anti-SDMA antibody associated with the solid matrix to determine the presence or amount of SDMA in the sample.

19. The method of claim 18, wherein the anti-SDMA antibody is labeled.

20. A solid phase comprising N-methylarginine (MMA) covalently attached to G6PDH, wherein the G6PDH is non-covalently attached to a particle.

21. The solid phase of claim 20, further comprising a porous matrix.

22. The solid phase of claim 21, wherein the porous matrix is mounted in a housing.

* * * * *